(12) United States Patent
Piskun et al.

(10) Patent No.: US 10,588,489 B2
(45) Date of Patent: Mar. 17, 2020

(54) ENDOLUMINAL SYSTEM AND METHOD FOR GASTROINTESTINAL TREATMENT

(71) Applicant: Boston Scientific Scimed, Inc., Maple Grove, MN (US)

(72) Inventors: Gregory Piskun, Morganville, NJ (US); John To, Newark, CA (US); Maríel Fabro, San Francisco, CA (US); Brian Tang, Fremont, CA (US); Sergey Kantsevoy, Owings Mills, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/230,455

(22) Filed: Aug. 7, 2016

(65) Prior Publication Data
US 2016/0338572 A1 Nov. 24, 2016

Related U.S. Application Data

(60) Continuation of application No. 14/506,666, filed on Oct. 5, 2014, which is a division of application No.
(Continued)

(51) Int. Cl.
*A61B 1/32* (2006.01)
*A61B 1/00* (2006.01)
(Continued)

(52) U.S. Cl.
CPC ...... *A61B 1/00085* (2013.01); *A61B 1/00087* (2013.01); *A61B 1/00154* (2013.01);
(Continued)

(58) Field of Classification Search
CPC ............ A61B 17/7032; A61B 17/7037; A61B 17/7002; A61B 17/7035; A61B 17/7068;
(Continued)

(56) References Cited

U.S. PATENT DOCUMENTS

| 457,787 A | 8/1891 | Leisenring |
| 1,621,159 A | 3/1927 | Evans et al. |

(Continued)

FOREIGN PATENT DOCUMENTS

| CN | 201200436 | 3/2009 |
| CN | 102018493 | 4/2011 |

(Continued)

OTHER PUBLICATIONS

European Search Report dated May 3, 2011 for European Patent Application No. 06789411.3.
(Continued)

*Primary Examiner* — Lynnsy M Summitt
*Assistant Examiner* — Tara Rose E Carter

(57) ABSTRACT

Improved methods and devices for performing an endoscopic surgery are provided. Systems are taught for operatively treating gastrointestinal disorders endoscopically in a stable, yet dynamic operative environment, and in a minimally-invasive manner. Such systems include, for example, an endoscopic surgical suite. The surgical suite can have a reversibly-expandable retractor that expands to provide a stable, operative environment within a subject. The expansion can be asymmetric around a stabilizer subsystem to maximize space for a tool and an endoscope to each be maneuvered independently to visualize a target tissue and treat the target tissue from outside the patient in a minimally invasive manner.

15 Claims, 20 Drawing Sheets

Related U.S. Application Data

13/862,346, filed on Apr. 12, 2013, now Pat. No. 9,186,130, which is a continuation of application No. 13/531,477, filed on Jun. 22, 2012, now Pat. No. 8,932,211, said application No. 14/506,666 is a continuation-in-part of application No. 13/726,147, filed on Dec. 23, 2012, now Pat. No. 9,161,746, which is a continuation of application No. 12/970,604, filed on Dec. 16, 2010, now Pat. No. 8,506,479.

(60) Provisional application No. 61/287,077, filed on Dec. 16, 2009.

(51) Int. Cl.
| | |
|---|---|
| *A61B 17/02* | (2006.01) |
| *A61B 1/31* | (2006.01) |
| *A61B 17/22* | (2006.01) |
| *A61B 17/00* | (2006.01) |
| *A61B 17/08* | (2006.01) |
| *A61B 17/10* | (2006.01) |
| *A61B 1/018* | (2006.01) |
| *A61B 17/221* | (2006.01) |

(52) U.S. Cl.
CPC .......... *A61B 1/00183* (2013.01); *A61B 1/018* (2013.01); *A61B 1/31* (2013.01); *A61B 1/32* (2013.01); *A61B 17/0057* (2013.01); *A61B 17/00234* (2013.01); *A61B 17/0218* (2013.01); *A61B 17/08* (2013.01); *A61B 17/10* (2013.01); *A61B 17/22* (2013.01); *A61B 17/221* (2013.01); *A61B 2017/003* (2013.01); *A61B 2017/2212* (2013.01)

(58) Field of Classification Search
CPC .............. A61B 17/7049; A61B 17/707; A61B 17/7041; A61B 17/705; A61B 17/7052; A61B 17/7071; A61B 2017/681; A61B 17/1757
USPC ........ 600/104, 109, 112–116, 121–125, 160, 600/203–212
See application file for complete search history.

(56) References Cited

U.S. PATENT DOCUMENTS

| | | | |
|---|---|---|---|
| 3,517,128 A | 6/1970 | Hines et al. | |
| 4,040,413 A | 8/1977 | Ohshiro | |
| 4,083,369 A | 4/1978 | Sinnreich | |
| 4,224,929 A | 9/1980 | Furihata | |
| 4,295,464 A | 10/1981 | Shihata | |
| 4,519,403 A | 5/1985 | Dickhudt | |
| 4,611,594 A | 9/1986 | Grayhack et al. | |
| 4,966,596 A | 10/1990 | Kuntz et al. | |
| 5,025,778 A | 6/1991 | Silverstein | |
| 5,059,199 A | 10/1991 | Okada | |
| 5,087,265 A | 2/1992 | Summers | |
| 5,112,310 A | 5/1992 | Grobe | |
| 5,197,971 A * | 3/1993 | Bonutti ............... | A61B 17/0218 604/105 |
| 5,386,817 A | 2/1995 | Jones | |
| 5,411,508 A | 5/1995 | Bessler et al. | |
| 5,423,830 A | 6/1995 | Schneebaum et al. | |
| 5,655,698 A | 8/1997 | Yoon | |
| 5,716,321 A | 2/1998 | Kerin et al. | |
| 5,722,103 A | 3/1998 | Walega | |
| 5,776,097 A | 7/1998 | Massoud | |
| 5,947,983 A | 9/1999 | Solar et al. | |
| 5,954,731 A | 9/1999 | Yoon | |
| 5,997,547 A | 12/1999 | Nakao et al. | |
| 6,009,877 A | 1/2000 | Edwards | |
| 6,042,596 A | 3/2000 | Bonutti | |
| 6,119,913 A | 9/2000 | Adams et al. | |
| 6,142,931 A | 11/2000 | Kunihide | |
| 6,142,933 A | 11/2000 | Longo et al. | |
| 6,203,552 B1 | 3/2001 | Bagley et al. | |
| 6,214,024 B1 | 4/2001 | Houser | |
| 6,264,086 B1 | 7/2001 | McGuckin et al. | |
| 6,302,311 B1 | 10/2001 | Adams et al. | |
| 6,343,731 B1 | 2/2002 | Adams et al. | |
| 6,405,732 B1 | 6/2002 | Edwards | |
| 6,423,058 B1 | 7/2002 | Edwards et al. | |
| 6,428,473 B1 | 8/2002 | Leonard et al. | |
| 6,494,881 B1 | 12/2002 | Bales et al. | |
| 6,616,603 B1 | 9/2003 | Fontana | |
| 6,695,198 B2 | 2/2004 | Adams et al. | |
| 6,805,273 B2 | 10/2004 | Bilotti et al. | |
| 6,808,491 B2 | 10/2004 | Kortenbach et al. | |
| 6,840,423 B2 | 1/2005 | Adams et al. | |
| 6,866,178 B2 | 3/2005 | Adams et al. | |
| 6,874,669 B2 | 4/2005 | Adams et al. | |
| 6,913,610 B2 | 7/2005 | Nakao | |
| 6,923,806 B2 | 8/2005 | Hooven et al. | |
| 6,938,814 B2 | 9/2005 | Sharma et al. | |
| 7,014,646 B2 | 3/2006 | Adams et al. | |
| 7,059,331 B2 | 6/2006 | Adams et al. | |
| 7,169,115 B2 | 6/2007 | Nobis et al. | |
| 7,276,066 B2 | 10/2007 | Ouchi | |
| 7,396,329 B2 | 7/2008 | Nakao | |
| 7,445,598 B2 | 11/2008 | Orban | |
| 7,918,787 B2 | 4/2011 | Saadat | |
| 7,959,559 B2 | 6/2011 | Yamaya | |
| 8,007,508 B2 | 8/2011 | Cox | |
| 8,277,373 B2 | 10/2012 | Maahs et al. | |
| 8,506,479 B2 | 8/2013 | Piskun et al. | |
| 8,517,933 B2 | 8/2013 | Mohr | |
| 8,608,652 B2 | 12/2013 | Voegele et al. | |
| 8,764,630 B2 | 7/2014 | Yamatani | |
| 8,777,961 B2 | 7/2014 | Cabrera et al. | |
| 8,932,326 B2 | 1/2015 | Riina et al. | |
| 8,979,884 B2 | 3/2015 | Milsom et al. | |
| 9,050,004 B2 | 6/2015 | Diao et al. | |
| 9,161,746 B2 | 10/2015 | Piskun et al. | |
| 9,168,053 B2 | 10/2015 | Cox | |
| 9,259,233 B2 | 2/2016 | Gruber et al. | |
| 9,370,379 B2 | 6/2016 | Osman | |
| 9,375,224 B2 | 6/2016 | Jansen | |
| 9,661,984 B2 | 5/2017 | Piskun | |
| 2001/0004947 A1 | 6/2001 | Lemke et al. | |
| 2001/0047169 A1 | 11/2001 | McGuckin et al. | |
| 2001/0049497 A1 | 12/2001 | Kalloo et al. | |
| 2002/0123748 A1 | 9/2002 | Edwards et al. | |
| 2002/0183593 A1 | 12/2002 | Chin et al. | |
| 2002/0193660 A1 | 12/2002 | Weber et al. | |
| 2003/0023143 A1 | 1/2003 | Abe et al. | |
| 2003/0050663 A1 | 3/2003 | Khachin et al. | |
| 2003/0074015 A1 | 4/2003 | Nakao | |
| 2003/0135230 A1 | 7/2003 | Massey et al. | |
| 2003/0225432 A1 | 12/2003 | Baptiste et al. | |
| 2003/0225433 A1 | 12/2003 | Nakao | |
| 2004/0034278 A1 | 2/2004 | Adams | |
| 2004/0082859 A1 | 4/2004 | Schaer | |
| 2004/0158263 A1 | 8/2004 | McAlister et al. | |
| 2004/0204725 A1 | 10/2004 | Bayer | |
| 2004/0249367 A1 | 12/2004 | Saadat et al. | |
| 2005/0177105 A1 | 8/2005 | Shalev | |
| 2005/0234297 A1 | 10/2005 | Devierre | |
| 2005/0234299 A1 | 10/2005 | Eitenmuller et al. | |
| 2005/0240147 A1 | 10/2005 | Makower et al. | |
| 2005/0251111 A1 | 11/2005 | Saito et al. | |
| 2005/0251177 A1 | 11/2005 | Saadat et al. | |
| 2005/0272977 A1 | 12/2005 | Saadat et al. | |
| 2006/0074277 A1 | 4/2006 | Yoshida | |
| 2006/0100480 A1 | 5/2006 | Ewers et al. | |
| 2006/0189845 A1 | 8/2006 | Maahs et al. | |
| 2006/0191975 A1 | 8/2006 | Adams et al. | |
| 2006/0247662 A1 | 11/2006 | Schwartz | |
| 2006/0264706 A1 | 11/2006 | Piskun | |
| 2007/0005093 A1 | 1/2007 | Cox | |
| 2007/0021778 A1 | 1/2007 | Carly | |
| 2007/0255207 A1 | 11/2007 | Hangai et al. | |

(56) References Cited

U.S. PATENT DOCUMENTS

| | | |
|---|---|---|
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyama et al. |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |
| 2008/0228209 A1 | 9/2008 | DeMello et al. |
| 2008/0249534 A1 | 10/2008 | Gruber et al. |
| 2008/0269557 A1* | 10/2008 | Marescaux et al. ... A61B 1/018 600/106 |
| 2008/0269559 A1 | 10/2008 | Miyamoto et al. |
| 2008/0275300 A1 | 11/2008 | Rothe et al. |
| 2008/0300454 A1 | 12/2008 | Goto |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2009/0287046 A1 | 11/2009 | Yamatani |
| 2009/0312645 A1 | 12/2009 | Weitzner et al. |
| 2010/0010296 A1 | 1/2010 | Piskun et al. |
| 2010/0049137 A1 | 2/2010 | Fisher, Jr. |
| 2010/0106240 A1 | 4/2010 | Duggal et al. |
| 2010/0152590 A1 | 6/2010 | Moore et al. |
| 2011/0065985 A1 | 3/2011 | Wehrheim |
| 2011/0077498 A1 | 3/2011 | McDaniel |
| 2011/0160538 A1 | 6/2011 | Ravikumar et al. |
| 2011/0172491 A1 | 7/2011 | Piskun et al. |
| 2011/0224494 A1 | 9/2011 | Piskun et al. |
| 2011/0245858 A1 | 10/2011 | Milsom et al. |
| 2011/0306832 A1 | 12/2011 | Bassan et al. |
| 2012/0083797 A1 | 4/2012 | Cabrera et al. |
| 2012/0095498 A1 | 4/2012 | Stefanchik et al. |
| 2012/0109178 A1 | 5/2012 | Edwards et al. |
| 2012/0165604 A1 | 6/2012 | Stokes et al. |
| 2013/0090527 A1 | 4/2013 | Axon |
| 2013/0172828 A1 | 7/2013 | Kappel et al. |
| 2013/0274553 A1 | 10/2013 | Piskun et al. |
| 2013/0317303 A1 | 11/2013 | Deshmukh et al. |
| 2013/0324795 A1 | 12/2013 | Nakajima et al. |
| 2014/0316379 A1 | 10/2014 | Sonderegger et al. |
| 2015/0150436 A1 | 6/2015 | Cornhill et al. |
| 2015/0157192 A1 | 6/2015 | Piskun et al. |
| 2015/0265268 A1 | 9/2015 | Diao et al. |
| 2015/0265818 A1 | 9/2015 | Piskun et al. |
| 2015/0272564 A1 | 10/2015 | Piskun et al. |
| 2015/0351890 A1 | 12/2015 | Levin et al. |
| 2016/0038172 A1 | 2/2016 | Cox |
| 2016/0081702 A1 | 3/2016 | Kan et al. |
| 2016/0106466 A1 | 4/2016 | Gruber et al. |
| 2016/0157843 A1 | 6/2016 | Dickson et al. |
| 2016/0374658 A1 | 12/2016 | Piskun |

FOREIGN PATENT DOCUMENTS

| | | |
|---|---|---|
| CN | 102695541 | 9/2012 |
| EP | 0163502 A2 | 12/1985 |
| EP | 1588670 A1 | 10/2005 |
| EP | 2512577 A2 | 10/2012 |
| GB | 2365340 | 2/2002 |
| JP | S63292935 | 11/1988 |
| JP | H08317928 A | 12/1996 |
| JP | H08336538 A | 12/1996 |
| JP | 2533732 | 4/1997 |
| JP | H1028691 | 2/1998 |
| JP | 2000166936 A | 6/2000 |
| JP | 2000-325303 | 11/2000 |
| JP | 2001527429 A | 12/2001 |
| JP | 2004154485 A | 6/2004 |
| JP | 2004529708 | 9/2004 |
| JP | 2005/046274 | 2/2005 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 | 4/2012 |
| JP | 2013514827 A | 5/2013 |
| JP | 2015525109 A | 9/2015 |
| WO | WO 1991/01773 | 2/1991 |
| WO | WO 1996/035469 | 11/1996 |
| WO | 9640347 A1 | 12/1996 |
| WO | 03000139 A1 | 1/2003 |
| WO | 2004103430 A2 | 12/2004 |
| WO | 2007081601 A2 | 7/2007 |
| WO | WO 2008/011163 | 1/2008 |
| WO | WO 2009/059296 | 5/2009 |
| WO | WO 2009/076176 | 6/2009 |
| WO | WO 2009/117696 | 9/2009 |
| WO | WO 2011/084616 | 11/2011 |
| WO | 2012068048 A1 | 5/2012 |
| WO | 2012114569 | 8/2012 |
| WO | 2013050880 A2 | 4/2013 |
| WO | 2013192116 | 12/2013 |
| WO | WO 2013/192116 | 12/2013 |
| WO | 2014200737 | 12/2014 |
| WO | 2015026968 A1 | 2/2015 |
| WO | 2015191125 A1 | 12/2015 |

OTHER PUBLICATIONS

European Search Report dated Jun. 1, 2014 for International Application No. PCT/US2014/040429.
Written Opinion dated Jun. 20, 2007 for International Application No. PCT/US06/30464.
Chinese Office Action dated May 12, 2009 for Chinese Application No. 200680028706.2.
International Search Report and Written Opinion dated May 6, 2016 for International Application No. PCT/US2016/016911.
International Search Report and Written Opinion (dated Dec. 14, 2017), for PCT/US17/50685 (16 pages).
The Extended PCT Search Report Application No. PCT/US2016/031355 dated Jul. 18, 2016.
European Communication for European Patent Application No. 14733912.1, dated Jun. 11, 2018, 2 pages.
International Search Report and Written Opinion dated May 9, 2018, PCT/US17/68991 ,11 pages.
International Search Report and Written Opinion for International Application No. PCT/US18/14388, dated Jun. 19, 2018, 9 pages.
International Search Report and Written Opinion for PCT/US10/60802, dated Aug. 24, 2011, 12 pages.
International Search Report and Written Opinion for International Application No. PCT/US18/21779, dated Jun. 14, 2018, 10 pages.
"Oleg Shikhmanvs. Bobcat Endoscopy, LLC(F/K/A/ LumenR LLC) and Gregory Piskun, M.D. Complaint", filed on Oct. 17, 2017, at Judicial District of Fairfield at Bridgeport, 25 pages.
"Oleg Shikhmanvs. Bobcat Endoscopy, LLC(F/K/A/ LumenR LLC) and Gregory Piskun, M.D. Reply to Affirmative Defenses, Matters in Avoidance and Answer to Counterclaims", dated Dec. 12, 2018, 19 pages.
"Oleg Shikhmanvs. Bobcat Endoscopy, LLC(F/K/A/ LumenR LLC) and Gregory Piskun, M.D., Answer, Special Defenses and Counterclaims", dated Sep. 13, 2018, 23 pages.
"Oleg Shikhmanvs. Bobcat Endoscopy, LLC(F/K/A/ LumenR LLC) and Gregory Piskun, M.D., First Amended Answer, Affirmative Defenses and Counterclaims", dated Nov. 9, 2018, 24 pages.
"Letter from Jeffrey M. Chamberlain, Senior Principal at Kacvinsky Daisak Bluni pllc to Michael J. Rye, Esq. c/o Cantor Colburn, LLP", dated Nov. 13, 2018, 3 pages.
"Letter from Michael J. Rye, Partner at Cantor Colburn LLP to Michael Mahoney, CEO at Boston Scientific Corporation", dated Oct. 17, 2017, 3 pages.

(56) References Cited

OTHER PUBLICATIONS

Letter from Michael J. Rye, Partner at Cantor Colburn LLP to Jeffrey M. Chamberlain at Kacvisky Daisak Bluni PLLC, dated Aug. 28, 2018, 2 pages.

* cited by examiner

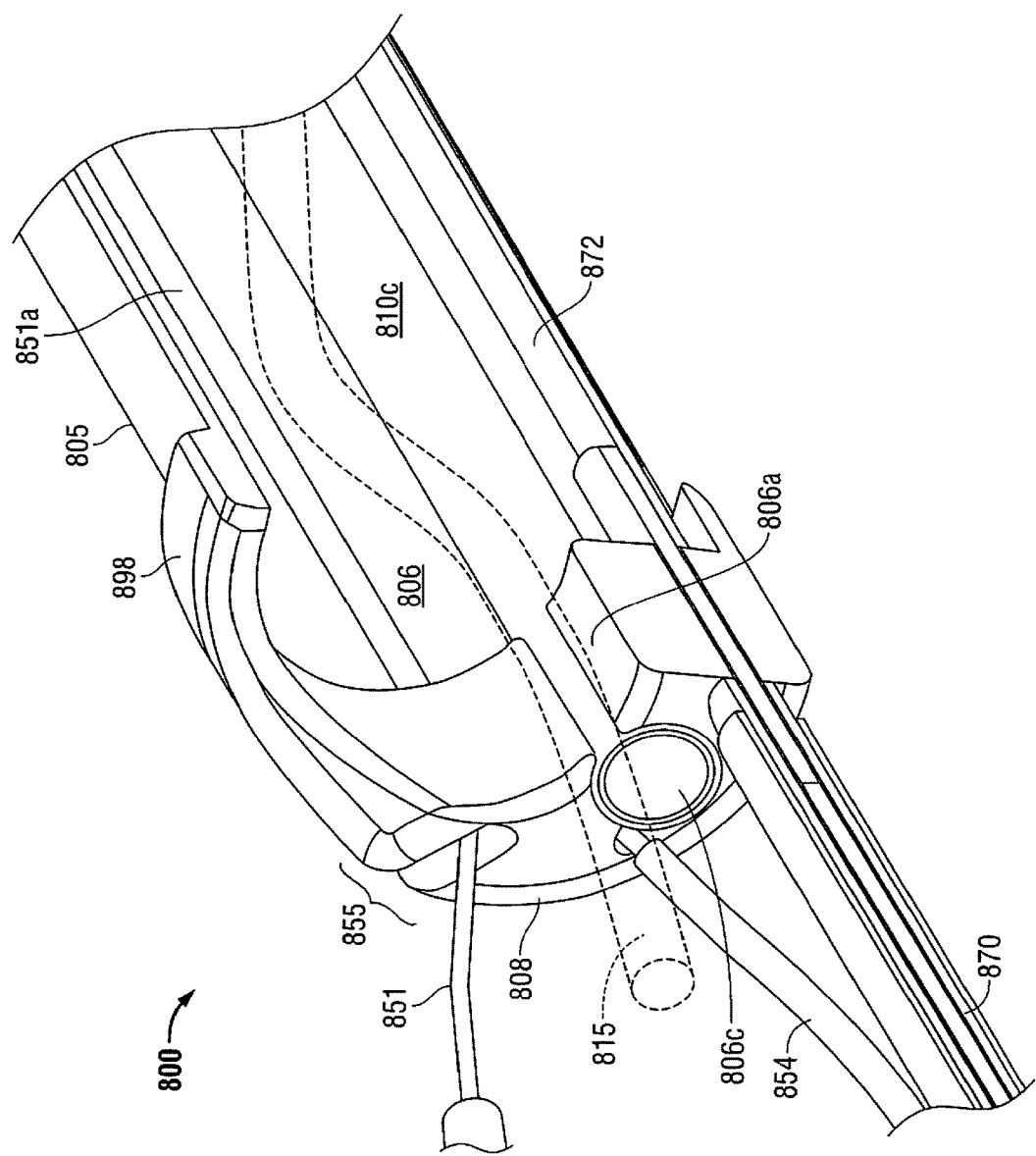

ENDOLUMINAL SYSTEM AND METHOD FOR GASTROINTESTINAL TREATMENT

This application is a continuation of application Ser. No. 14/506,666, filed Oct. 5, 2014, which is a divisional of application Ser. No. 13/862,346, filed Apr. 12, 2013, now U.S. Pat. No. 9,186,130, which is a continuation of application Ser. No. 13/531,477, filed Jun. 22, 2012, now U.S. Pat. No. 8,932,211, and is a continuation-in-part of application Ser. No. 13/726,147, filed Dec. 23, 2012, now U.S. Pat. No. 9,161,746, which is a continuation of application Ser. No. 12/970,604, filed Dec. 16, 2010, now U.S. Pat. No. 8,506,479, which claims priority from provisional application Ser. No. 61/287,077, filed Dec. 16, 2009. The entire contents of each of these applications are incorporated herein by reference.

BACKGROUND

Field of the Invention

The teachings provided herein are generally directed to improved methods and devices for operatively treating gastrointestinal disorders endoscopically in a stable, yet dynamic operative environment, and in a minimally-invasive manner.

Description of the Related Art

Endoscopic procedures involving the gastrointestinal system offer advantages over conventional surgery in that they are less invasive and provide direct visualization. These procedures continue to evolve to address problems and provide new methods of treatment identified by those skilled in the art.

One current problem includes a lack of technology for an optimal minimally-invasive expansion of a stable, working space adjacent to the target tissues that could otherwise collapse around the target lesion or defect during an operative treatment. Having the ability to effectively expand and optimally reconfigure the working space could markedly facilitate an intra-luminal operation. A better expanded, stable and optimally configured working space allows the instruments and endoscope to be independently manipulated and properly visualized around the target tissue. One of skill would appreciate having the ability to see and approach both the target tissue and the surrounding anatomy for reference, orientation, and surgical maneuvering.

Another current problem includes a lack of an endoscopic technology for not only expanding, but also affixing and stretching, both the target tissue and surrounding tissue. In a bowel, for example, such a stable operative space could include a space that is non-collapsible, with limited peristalsis or aperistaltic, and/or affixed at a particular point in the abdominal cavity. The fixed point can be considered fixed in relation to, for example, a fixed body point in the patient, such as the patient's hip. Significant bowel movement is considered to be highly undesirable during an operation on the bowel, for example, since it may create a challenging, unstable operative environment. Such bowel movement is normal, of course, even in a sedated patient and can be caused, for example, by bowel collapse from an air leak, peristalsis, breathing, and movement of the scope and instruments. Having a technology to overcome this problem would help provide a stable operative space, which is clinically desired by one of skill in the operative environment.

Another current problem includes a lack of an endoscopic technology for retracting the tissue dynamically, for example, through an adjustable tissue retraction structure allowing for a controlled degree of expansion or collapse of the structure, to further configure the working space as desired between the instruments and target tissue. Such control can effectively provide for a method of adjusting the retractor, as well as tissue placement, in-and-around the working space. By increasing and releasing the tension on the retractor, the amount of tissue to be placed in the working space, for example, can be better-gauged and controlled during a procedure. Moreover, the tissue retraction and, particularly, traction-contra-traction can be facilitated to help create a desired dissecting plane or position the tissue more optimally during an operation. Having a technology to overcome this problem would help create an operative environment that is more desirable for tissue dissection, retraction, cutting and a removal of tissue.

Another current problem includes a lack of an endoscopic technology for organizing the endoscope, instruments, and working space in a manner that can maximize the working space for the treatment. The larger space can improve the ability to manipulate the instruments and endoscope in a minimally-invasive manner from outside the body. Namely, one of skill would like to have a working space that has a point of entry for the instruments that is as far as practical from the target tissue to provide additional flexibility in approaching and visualizing the target tissue, perhaps providing more operating room for selecting a trajectory of the instruments toward the target tissue that is, for example, at least substantially perpendicular to the plane of dissection of the target tissue. Having a technology to overcome this problem would provide the person of skill with a system and procedure that is more desirable for a removal of tissue.

In view of at least the above, one of skill in the art of endoscopic, gastrointestinal surgical treatments would appreciate the technology taught herein which provides (i) a minimally-invasive expansion of target tissues; (ii) an affixing, particularly an affixing that includes a reconfiguring without stretching or reconfiguring with stretching, of both the target tissue and surrounding tissue to help provide a stable, operative space; (iii) a retracting of the tissue dynamically, allowing for a partial or complete expansion or collapse, to further configure the working space between the instruments and the target tissue; and (iv) an organization of the endoscope instruments, such as the retractor and tools to maximize the working space and maneuverability, allowing for a maximum flexibility in approaching and visualizing the target tissue. It should be appreciated that having such improvements would reduce the technical complexity, and increase the efficacy and safety of, otherwise complex endoscopic operations. Moreover, doing so at a low cost, while using an affordable system that is introduced in the subject atraumatically and in a manner that does not substantially disrupt the conventional colonoscopy workflow, would be seen by those of skill as a very substantial advancement in the field endoscopic surgical procedures.

SUMMARY

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite. The surgical suite can have a reversibly-expandable retractor that expands to provide a stable, operative environment within a subject. The expansion can be asymmetric around a stabilizer subsystem to maximize space for a tool and an endoscope to each be maneuvered independently to visualize a target tissue and treat the target tissue from outside the patient in a minimally invasive manner. Embodiments taught herein provide, among other improvements, an increase in distance between tool ports and the target tissue to improve maneuverability and triangulation of the tools with respect to the target tissue, as well as a larger field of view.

The teachings include a floating, multi-lumen-catheter retractor system for ease of positioning in a subject. These systems are designed to provide a minimally invasive treatment of the subject. In some embodiments, the systems comprise a highly flexible outer tube configured for guiding a floating channel and a floating endoscope in an at least substantially floating arrangement within the system. This flexible outer tube can have a lumen, a proximal end, and a distal end. And, during a use of the system, the floating channel can serve as a guide through which a tool is manipulated in a treatment of a target tissue in a subject. In some embodiments, the tool can include a grasper, a forcep, a snare, a clamp, a scissor, a knife, a dissector, an endoscopic stapler, a tissue loop, a clip applier, a suture-delivering instrument, or an energy-based tissue coagulator or cutter. And, in some embodiments, the floating channel can have an elevator component for moving a bendable section to manipulate the tool.

The system can also comprise a stable, yet dynamic operative environment in that it can include a reversibly-expandable retractor that expands to form a treatment space in the subject. The retractor can be configured, for example, for the expansion to occur distal to the distal end of the outer tube and at least substantially render the target tissue aperistaltic for the treatment. During the use of the system, the floating channel can be at least substantially attached to the lumen of the outer tube at a first proximal location and a first distal location, and be at least substantially floating in the lumen of the outer tube between the first proximal location and the first distal location. Likewise, during the use of the system, the floating endoscope can be at least slidably-attached to the lumen of the outer tube at a second proximal location and a second distal location, and be at least substantially floating in the lumen of the outer tube between the second proximal location and second distal location. And, during the use of the system, the at least substantially floating arrangement can at least substantially increase the flexibility of the system over a second such system, the second such system having a lumen for a tool and an endoscope affixed to the lumen throughout the length of the outer tube between the proximal end and the distal end of the outer tube. The increased flexibility of the at least substantially floating arrangement can facilitate an ease of positioning the system in the subject for the treatment of the target tissue.

In some embodiments, the retractor can be a reversibly-stabilized and reversibly-expandable retractor, retractor forming an asymmetrical treatment space upon the expansion. And, the retractor can be configured to reversibly stiffen an otherwise flexible arrangement of the retractor, the flexible arrangement designed to facilitate the ease of positioning of the system in the subject and to reversibly stiffen for the expansion of the retractor.

The teachings also include a multi-lumen catheter system having a reversibly-stabilized and reversibly-expandable retractor for a minimally invasive treatment of a subject. The system can comprise a flexible outer tube for guiding a channel and an endoscope within the system, the flexible outer tube having a lumen, a proximal end, and a distal end. The channel serves as a guide through which a tool is manipulated in a treatment of a target tissue in a subject. In some embodiments, the retractor can be a reversibly-stabilized and reversibly-expandable retractor forming a treatment space upon expansion and configured for the expansion to occur distal to the distal end of the outer tube. The retractor can be designed to reversibly-stiffen an otherwise flexible arrangement of the retractor, the flexible arrangement designed to facilitate the positioning of the system in the subject and to reversibly stiffen for the expansion of the retractor. In these embodiments, the reversibly-stiffened arrangement of the retractor can form an at least substantially rigid beam as a structural support for the expansion.

During a use of the system, the channel can be a floating channel that is (i) at least substantially attached to the lumen of the outer tube at a first proximal location and a first distal location and (ii) at least substantially floating in the lumen of the outer tube between the first proximal location and the first distal location. Likewise, during the use of the system, the endoscope can be a floating endoscope that is (iii) at least slidably-attached to the lumen of the outer tube at a second proximal location and a second distal location and (iv) at least substantially floating in the lumen of the outer tube between the second proximal location and second distal location. And, during the use of the system, the channel and the endoscope form an at least substantially floating arrangement that (v) at least substantially increases the flexibility of the system over a second such system having separate lumens for a tool and an endoscope, the separate lumens affixed to the lumen throughout the length of the outer tube between the proximal end and the distal end of the outer tube, the increased flexibility facilitating an ease of positioning the system in the subject for the treatment of the target tissue.

The teachings also include a surgical suite with a floating, multi-lumen-catheter retractor system having a reversibly-stabilized and reversibly-expandable retractor for a minimally invasive treatment of a subject. In these embodiments, the system can comprise a highly flexible outer tube for guiding a floating channel and a floating endoscope in an at least substantially floating arrangement within the system. The flexible outer tube can have a lumen, a proximal end, and a distal end; and, the floating channel can serve as a guide through which a tool is manipulated in a treatment of a target tissue in a subject. The retractor can be a reversibly-stabilized and reversibly-expandable retractor forming a treatment space upon expansion. The retractor can be configured, for example, for the expansion to occur distal to the distal end of the outer tube and to reversibly stiffen an otherwise flexible arrangement of the retractor, the flexible arrangement designed to facilitate the positioning of the system in the subject and to reversibly stiffen for the expansion of the retractor.

During a use of the system, the floating channel can be (i) at least slidably-attached to the lumen of the outer tube at a first proximal location and a first distal location and (ii) at least substantially floating in the lumen of the outer tube between the first proximal location and the first distal location. Likewise, during the use of the system, the floating endoscope can be (iii) at least slidably-attached to the lumen of the outer tube at a second proximal location and a second distal location; and, (iv) at least substantially floating in the lumen of the outer tube between the second proximal location and second distal location. And, during the use of the system, the at least substantially floating arrangement can (v) at least substantially increase the flexibility of the system over a second such system having lumens for a tool and an endoscope, the lumens affixed to the lumen of the outer tube throughout the length between the proximal end and the distal end of the outer tube. The increased flexibility can facilitate an ease of positioning of the system in the subject; and, the reversibly-stiffened arrangement of the retractor can form an at least substantially rigid beam as a structural support for the expansion in the subject for the treatment of the target tissue.

In some embodiments, the retractor comprises at least two expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a distal nexus located distal to the distal end of the outer tube and at which the distal end of each of the at least two retractor elements is affixed; and, a stabilizer subsystem connecting the distal nexus to the distal end of the outer tube and having an at least substantially rigid component configured to reversibly stiffen an otherwise flexible portion of the retractor for an asymmetric expansion of the retractor.

In some embodiments, the retractor comprises four expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a proximal coupler attached to the distal end of the outer tube, the proximal coupler having four retractor ports for the slidable engagement with the four retractor elements, the four retractor ports positioned circumferentially around the proximal coupler and configured to facilitate a reversible, axial sliding of the retractor elements for the asymmetric expansion of the retractor. These embodiments can also include a distal nexus located distal to the distal end of the outer tube and at which the distal ends of each of the four retractor elements are affixed; and, a stabilizer subsystem connecting the distal nexus to the distal end of the outer tube and having (i) a flexible component that extends from the proximal coupler to the distal nexus and (ii) an at least substantially rigid component that is slidably engaged with the proximal coupler and reversibly extends from the proximal coupler to the distal nexus to reversibly-stiffen the retractor in an asymmetric expansion of the retractor.

The flexible component and the rigid component can have central axes that are each at least substantially parallel to the central axis of the distal end of the shaft, the rigid component forming an at least substantially rigid beam as a structural support for the asymmetric expansion, the rigid beam having a luminal side and an abluminal side. And, the expansion can occur in a disproportionally greater amount on the luminal side of the rigid beam to increase the treatment space, the treatment space having a volume that is asymmetrically distributed around the rigid beam. In some embodiments, the expansion can occur in an amount that is at least 5× greater on the luminal side of the beam than the abluminal side of the beam.

In some embodiments, the system can include a bridge member configured to maintain a desired orientation of the retractor elements during the expansion, the bridge member operably stabilizing at least two of the four retractor elements. Moreover, in some embodiments, the outer tube can be wire-reinforced to provide kink resistance and torqueability to the system to further facilitate a positioning of the system in the subject.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; improving visualization, for example, some lesions can be seen much better when tissue is retracted and stabilized; optimally positioning the target tissue in relation to the tool, for example, by optimizing the position of the duodenal papilla, facilitating its cannulation during a procedure; treating the target tissue with the tool; collapsing the retractor; and, withdrawing the system from the subject. The lesion can include, for example, a perforation, a tissue pathology a polyp, a tumor, a bleed, a diverticuli, an ulcer, a cancerous tissue, an abnormal vessel, or an appendix.

BRIEF DESCRIPTION OF THE FIGURES

FIG. 8 illustrates the cutaway view of FIG. 7, showing the distal end of the outer tube of a system as taught herein, in which components of the system can be floating in the outer tube to enhance flexibility for positioning the system in a subject, according to some embodiments.

DETAILED DESCRIPTION

Figure 1:
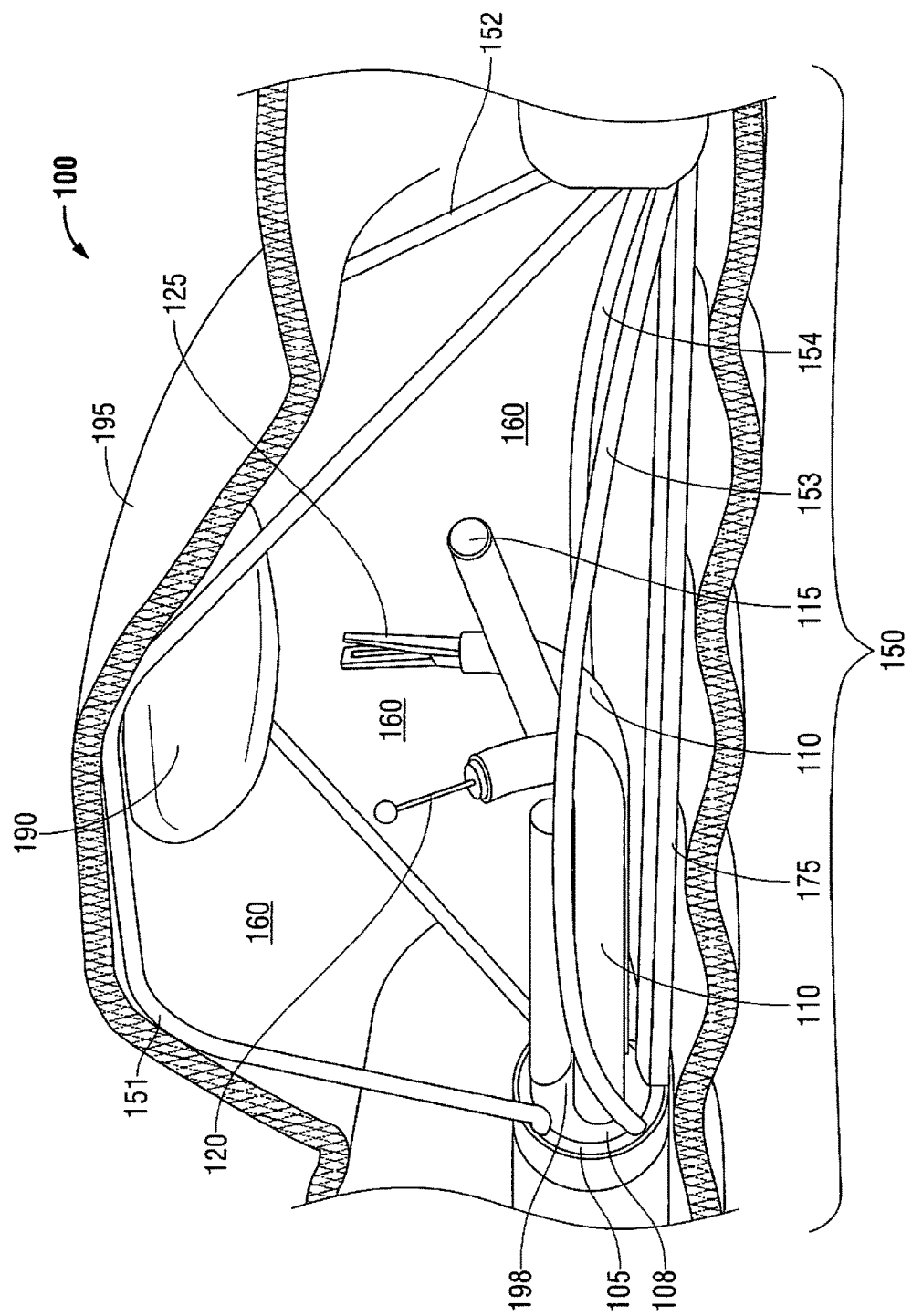
FIG. 1 illustrates a system for operatively treating gastrointestinal disorders endoscopically in a stable, yet dynamic operative environment, and in a minimally-invasive manner, according to some embodiments.

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite. The surgical suite can have a reversibly-expandable retractor that expands to provide a stable, operative environment within a subject. In some embodiments, the expansion can be asymmetric around a stabilizer subsystem to maximize space for a tool and an endoscope to each be maneuvered independently to visualize a target tissue and treat the target tissue from outside the patient in a minimally invasive manner. Embodiments taught herein can provide, among other improvements, an increase in distance between tool ports and the target tissue to enhance the independent maneuverability and triangulation of each of the tools with respect to the target tissue. This increase in distance can also provide a way of obtaining a larger field of view. The systems taught herein, for example, can (i) enable a working space to be dynamically configured around the target tissue in tortuous body lumens and orifices such as the gastrointestinal tract using controls from outside the body; (ii) provide a flexible, passageway for multiple surgical tools and instruments, such as endoscope and graspers to be passed from outside the body towards the target tissues; (iii) organize and/or constrain tools in the working space; (iv) at least substantially immobilize and/or stabilize the target tissue and surrounding tissue for a treatment; and/or (v) enable control over the geometry position, and orientation of the instruments such as the grasper in the working space from outside the body.

The terms "treat," "treatment", and "treating" include, for example, the therapeutic and/or prophylactic uses in the prevention of a disease or disorder, inhibition of a disease or disorder, and/or amelioration of symptoms of disease or disorder. The term "subject" and "patient" can be used interchangeably and refer to an animal such as a mammal including, but not limited to, non-primates such as, for example, a cow, pig, horse, cat, dog, rat, and mouse; and, primates such as, for example, a monkey or a human.

In some embodiments, the systems taught herein can include dynamically reconfigurable, asymmetric retractor structures on the distal end of a flexible and torque-able multi-channel shaft having a handle that allows for control over both the stiffness and geometry of the working space formed by the expansion of the retractor. In some embodiments, the retractor can include a stabilizer subsystem having 2-8, 3-5, 4-6, or any range therein, flexible retractor elements. In some embodiments, the retractor elements can be aligned at least substantially parallel to each other when fully collapsed for positioning in the patient. In some embodiments, the retractor elements are aligned on planes that are within about 5-30 degrees, about 10-25 degrees, about 15-20 degrees, about 15 degrees, or any range therein, of each other, in some embodiments. In some embodiments, the retractor elements form a frame that has a length ranging from about 4-12 cm. 6-10 cm, 7-9 cm, 5-11 cm, or any range therein. In some embodiments, the frame is about 8 cm long. In some embodiments, the retractor elements form a frame that has a width ranging from about 1-5 cm. 2-4 cm, or any range therein. In some embodiments, the frame is about 3 cm wide. In some embodiments, the retractor elements form a frame that has a height ranging from about 1-5 cm. 2-4 cm, or any range therein. In some embodiments, the frame is about 3 cm high. One of skill will appreciate that there are a number of suitable materials that can be used to make the retractor elements for the purposes set-forth herein. In some embodiments, the retractor elements can be made from NITINOL. In some embodiments, the retractor element can comprise, multifilament steel wires or polymer cords. The polymer materials can include polyetheretherketone (PEEK), nylon, polyester, polycarbonate, polyurethane, or polyethylene. The gauge of the retractor elements can vary, depending on material. In some embodiments, the retractor elements can comprise wires that range from about 0.020"-0.40" in diameter. In some embodiments, the retractor elements are 0.030" in diameter.

The term "about" is used in the teachings herein to describe possible variations in amounts or ranges that can be used in embodiments. It can be used in embodiments, for example, to include the exact amount or range specified, as well as a variation of which that would not create a substantial difference in function. A difference in function can be insubstantial, for example, where it is less than 20% in some embodiments, less than 15% in other embodiments, less than 10% in yet other embodiments, or perhaps even less than 5% in yet other embodiments. One of skill will appreciate that the percentage difference in function required for to be substantial will depend on the function of the embodiment itself that is under comparison.

The methods, devices, and systems taught herein can be used for minimally-invasive procedures. A non-invasive procedure, in contrast, can be defined as a procedure that includes no violation of the skin or the mucosa, and no appreciable damage to any other tissues of the body. A minimally-invasive surgical operation, on the other hand, involves minimal access trauma and minimal collateral tissue damage during a surgical operation. The terms "minimal," "minimize," "minimizing," "minimized," "avoid," "avoiding," "avoided," can be used interchangeably in some embodiments. Minimally-invasive surgery is desirable, for example, to reduce trauma to the patient, speed the healing process, reduce risk and, thus, reduce the length and expense of a hospital stay by minimizing or avoiding tissue damage, or risk of tissue damage. Tissue damage, or the risk thereof, can be minimized or avoided, for example, where a procedure is designed to minimize or avoid unnecessary tissue contact that may otherwise be associated with a procedure. The gentle procedures taught herein, for example, are directed to preserving tissue during a gastrointestinal surgery.

The systems taught herein can be dynamic in some embodiments, for example, such that the tissue retraction can include partial or complete expansion or collapse of a retractor to facilitate an increase or decrease in the distance between instruments and the target tissue, which is useful in reconfiguring the work space and aiding in axial movements of the tools. By increasing and releasing the tension, the amount of tissue to be placed in the working space can also be better-gauged during a procedure, for example, and tissue traction-contra-traction can be facilitated to help in creating a dissecting plane during a removal of tissue. One of skill will appreciate having the ability to dynamically reconfigure the working space and optimize traction-contratraction on the target tissue, as this can facilitate surgical manipulations.

FIG. 1 illustrates a system for operatively treating gastrointestinal disorders endoscopically in a stable, yet dynamic operative environment, and in a minimally-invasive manner, according to some embodiments. The system 100 can include a multi-lumen-catheter retractor system for ease of positioning in a subject, and such systems can be designed to provide a minimally invasive treatment of the subject. The system 100 can have a flexible outer tube 105 configured for guiding a channel 110 and an endoscope 115 within the system 100. The flexible outer tube 105 can have a lumen (not shown), a proximal end (not shown), and a distal end (not shown) to house, for example, the channel and the endoscope during use of the system 100. As such, the outer tube can be a multi-luminal tube, in some embodiments. And, during the use of the system 100, the channel 110 can serve as a guide through which a tool 120, 125 can be manipulated in a treatment of a target tissue 190 in the gastrointestinal tract 195 of the subject. The channel 110 can, for example, be in operable contact with an independently manipulable-and-articulable tool, the channel having an elevator component for moving a bendable section.

In some embodiments, the tool can be any tool known to one of skill. For example, the tool 120, 125 can include a grasper, a forcep, a snare, a scissor, a knife, a dissector, a clamp, an endoscopic stapler, a tissue loop, a clip applier, a suture-delivering instrument, or an energy-based tissue coagulator or cutter. And, in some embodiments, the channel 110 can have an elevator component (not shown) for moving a bendable section, often a distal end of the channel 110, to manipulate the tool 120, 125. In some embodiments, at least one channel 110 and/or the endoscope 115 can have at least substantial freedom to move within the outer tube 105 during operation, or "float," such that the system 100 can be considered to be a floating, multi-lumen-catheter retractor system. It should be appreciated that the terms "tool" and "instrument" can be used interchangeably in some embodiments taught herein.

In some embodiments, the system can comprise a stable, yet dynamic operative environment in that it can include a reversibly-expandable retractor 150 that expands to form a treatment space 160 in the subject. The retractor 150 can be configured, for example, for the expansion to occur distal to the distal end 108 of the outer tube 105. In some embodiments, the retractor can at least substantially render the target tissue 190 aperistaltic for the treatment. The retractor 150 can have a variety of configurations to serve, for example, as a scaffolding within the gastrointestinal tract 195. For example, the retractor 150 can include retractor elements 151, 152, 153, 154, along with a proximal coupler 198 operably connected to the retractor elements 151, 152, 153, 154, whether at least substantially attached and/or at least slidably-engaged to the retractor elements 151, 152, 153, 154, and a distal nexus 199 for a distal point of an operable connection with the retractor elements 151, 152, 153, 154.

Moreover, the retractor 150 can be a reversibly-stabilized and reversibly-expandable retractor, the retractor 150 forming an asymmetrical treatment space 160 upon the expansion. And, the retractor 150 can be configured to reversibly stiffen an otherwise flexible arrangement of the retractor 150, the arrangement designed to facilitate ease of positioning of the system 100 in the subject and to reversibly stiffen for the expansion of the retractor 150. The stabilization of the retractor 150 can, in some embodiments, include a means for stabilizing the retractor 150 through a stabilizer subsystem as taught herein, the stabilizer having, for example, an at least substantially-rigid beam 175 to support the expanded retractor 150.

In some embodiments, the outer tube can have any dimensions believed to be useful to one of skill for the purposes taught herein. For example, the outer tube can have an outer diameter ranging from about 3 mm to about 30 mm, about 5 mm to about 25 mm, about 7 mm to about 22 mm, from about 9 mm to about 20 mm, from about 11 mm to about 18 mm, from about 8 mm to about 15 mm, from about 10 mm to about 16 mm, or any range therein in increments of 1 mm. The length of the outer tube can range, for example, from about 30" to about 72", from about 31" to about 36", from about 28" to about 80", from about 32" to about 40", from about 34" to about 38", or any range therein in increments of 1".

The outer tube can be manufactured from any materials know to be useful to one of skill for the purposes taught herein. For example, the out tube can comprise a polymer, or perhaps a polymer having an embedded wire reinforcement. The wire reinforcement can be a mesh, a braid, a helical coil or any combination thereof. The wire reinforcement can include any material believed by one of skill to be useful for the purposes set-forth herein. For example, wire reinforcement can comprise a material having an elastic modulus that is about 1-3 orders of magnitude higher than the polymer tube. The wire material can comprise, for example, a stainless steel having a diameter ranging from about 0.003" to about 0.017", about 0.005" to about 0.015", about 0.010" to about 0.012", or any range therein in increments of about 0.001". The tube hardness, or durometer, can be any of that which one of skill will find useful for the purposes set forth herein. For example, the hardness can range, for example, from about 50 Shore A to about 60 Shore A, about 40 Shore A to about 80 Shore A, about 45 Shore A to about 70 Shore A, or any range therein in increments of 1 Shore A. One of skill will appreciate that the outer tube should be flexible, elastically bendable, but sufficiently stiff torsionally to transmit torque from the handle or proximal end of the system to the retractor or distal end of the system.

The outer tube can be connected to a ring distally, referred to herein as the proximal coupler in some embodiments, which can have portals for retractor elements to slide through, as well as a desired orientation and positioning of the channels for the endoscope and at least one tool, such that the retractor elements, endoscope, and at least one tool are organized relative to each other in a predetermined manner to achieve a particular function, such as an increase in working space, a better view of a plane of dissection, or any other procedural variable deemed of interest to one of skill.

In some embodiments, the retractor structures taught herein are each a means for substantially immobilizing the lesion to the extent desired for the treatment. For example, the current use of loops and a piece-meal removal of flat or wide-based polyps, such as those having a base of about 1 cm or wider, may not provide clear surgical margins, whereas the systems taught herein can, in some embodiments, immobilize or affix the entire circumference of the bowel wall around the treatment area and facilitate the production of clear surgical margins. One of skill will appreciate having a working space that can be provided by the systems taught herein, the working space being (i) at least substantially non-collapsible, (ii) at least substantially aperistaltic; and, (iii) at least substantially affixed at a particular point in the abdominal cavity in relation to any fixed body point, like a hip, for example. This is a significant improvement over existing systems, as existing systems have not addressed many existing problems including, for example, bowel collapse that can result from an air leak from the working space; peristalsis that is normal, even in a sedated patient; and, additional undesired bowel movements caused by the patient's breathing, movement of the scope or other instrument manipulation, or perhaps even by a surrounding peristalsis causing movement at a treatment area. Such problems are addressed by systems taught herein. As such, systems taught herein can offer a rigid, stable structure having at least substantial resistance to a variety of moving forces in the abdomen that are typically present during a gastrointestinal endoscopic procedure. One of skill will appreciate decreasing the effects of these moving forces on the working space to help reduce otherwise inherent technical complexities, limited efficacies, and decreased safety during endoscopic procedures.

In some embodiments, the systems taught herein can be slidably positioned over an endoscope during use. In fact, it should be appreciated that there are a variety of methods of using systems taught herein that are already used by one of skill in current state-of-the-art procedures. For example, the method can include inserting the multi-luminal tube into an overtube, cover, or sheath. And, in some embodiments, the endoscope can be a colonoscope. In many embodiments, regardless of the method of use, the retractor structures can mechanically retract one side of the colonic wall in an asymmetric manner to increase the distance between the target lesion and the opposite wall, as well as between the lesion and the instruments in their most retracted, but visualized, position to increase the effective work space.

In some embodiments, the systems can include a multi-lumen catheter having at least 2 working channels for manipulating tools and an endoscope, each of the two working channels having 6 degrees of freedom that are independent from each other and the endoscope. The ability to independently manipulate the endoscope and tools allows, for example, one instrument to retract the tissue or lesion away or substantially perpendicular to another instrument, for example, the dissecting instrument, while independently optimizing the endoscope's position and, hence, the view of the treatment area. This would facilitate the removal of tissue with clear margins. The channels can manipulate the tools with several degrees of freedom, 6 degrees of freedom in some embodiments, providing a greatly enhanced maneuverability in the working area when compared to current state-of-the-art systems. In some embodiments, the at least one independently manipulable-and-articulable tool can be independently rotatable to an angle of up to about 360 degrees, about 315 degrees, about 270, about 225 degrees, about 180 degrees, about 135 degrees, or about 90 degrees in the working area. In addition the tools can be independently bendable to an angle of up to about 180 degrees, about 135 degrees, about 90 degrees, or about 45 degrees in at least one direction in the working area.

The systems taught herein can have a means for organizing the orientation of the floating channels, in order to further facilitate improving the flexibility of the system. In some embodiments, for example, the proximal coupler, the ring that can be attached to the distal end of the outer tube, can be used to organize the tools and endoscope in a particular arrangement to facilitate a particular positioning of the tools as they emerge from the shaft into the working space created by the retractor. In some embodiments, the tool channels can be placed further than the endoscope from the retractor elements that expand the most. Likewise, the proximal end of the outer tube can also have respective openings for each of the channels, and these openings can be, for example, a part of a handle coupler, or the handle itself, operably connecting one or more of the channels to the outer tube. The operable connection between the outer tube and channels can provide a means for controlling the endoscope and tools, for example, from outside the patient. The rings can be made of any material believed by one of skill to be suitable for the purposes discussed herein. For example, the rings can be made of stainless steel, or perhaps a plastic such as polycarbonate or acrylonitrile butadiene styrene (ABS).

It should be appreciated that, in some embodiments, the systems taught herein can include any combination of components, the selected combination of which is designed to be operable with components that are obtained separate from the system. For example, the system can include an outer tube and a retractor component, the outer tube being operable with at least one channel obtained separately and an endoscope obtained separately. Likewise, the system can include an outer tube, a retractor, and an endoscope, and the channels are obtained separately; or an outer tube, a retractor, and a channel, the endoscope obtained separately. Moreover, the system can include an outer tube, a retractor, an endoscope, and at least one channel; or, a handle, an outer tube, a retractor, an endoscope, at least one channel, and at least one tool.

The terms "substantial," and "substantially" can be used, for example, to refer to a relative measure for a parameter. It can be used in some embodiments, for example, to refer to a degree of change or function that relates to an amount, a performance, or some other characteristic. The following are for purposes of example in describing general embodiments: As described, the systems can be considered to be floating systems, can have a floating channel, a floating endoscope, multiple floating channels, or a combination thereof, in some embodiments. For example, the phrase, "an at least substantially floating arrangement within the system", can refer to an arrangement, for example a channel or endoscope arrangement, that can have some attachment that restricts movement in at least one direction, a minimal attachment to minimize such restriction of movement, or perhaps no attachment at all, to another system component. For example, a channel or endoscope can be arranged to be at least substantially floating in the outer tube relative to a second such system that does not use a floating-type arrangement to increase flexibility, or inherently achieve an increase in flexibility, of the second such system. As such, in many embodiments, the endoscope and/or channel can have a substantial portion of its arrangement unattached within the system, allowing the substantial portion to "float" or move substantially freely within the outer tube. The "substantial portion" can be, for example, a percentage of the arrangement that must remain unattached within the system to provide a performance characteristic, such as an increased flexibility of the system when compared to the second such system that does not use a floating-type arrangement to increase flexibility, or inherently achieve an increase in flexibility, of the second such system.

The phrase, "at least substantially render the target tissue aperistaltic for the treatment", for example, can refer to the target tissue having some minimal peristalsis, or perhaps no peristalsis, under the conditions of normal use to provide a performance characteristic, such as controlling movement of the target tissue to facilitate treatment. The phrase, "at least substantially attached", for example, "at least substantially attached to the lumen of the outer tube", for example, can refer to a component having a fixed attachment or moveable attachment. In some embodiments, the attachment can be between the component and the lumen, such that there is a loss of at least one degree of freedom of movement of the component. For example, the component can slide and/or rotate in relation to the lumen of the outer tube, as long as the sliding and/or rotating occur in relation to a particular fixed point on the lumen. Likewise, "at least substantially attached" can, of course, mean "fixed", "reversibly fixed," or the like, in some embodiments. Likewise, "at least slidably-attached" can refer to an attachment between components that allows for at least sliding motion between components such as, for example, a sliding motion between a port and a tube. In some embodiments, an endoscope can be at least slidably-attached, for example, where the scope is allowed to slide in the direction of the scope's central axis in and out of a port, such that the distance that the scope extends beyond the port is adjustable. And, in some embodiments, a component can be "at least slidably-attached" where it can slide as well as move in other directions. For example, the port can be substantially larger than the scope, in some embodiments, such that the scope can slide axially, as well as move side-to-side, align its central axis parallel to the central axis of the outer tube, or perhaps, misalign it's central axis to not be parallel to the central axis of the outer tube.

The phrase, "at least substantially increases the flexibility" can refer to an orientation of components that enhances the flexibility of a system when compared to another orientation and design of the components. For example the phrase "at least substantially increases the flexibility of the system over a second such system" can refer to a comparison of flexibility of the claimed system over the second system not having the floating arrangement under the conditions of normal use, such that the flexibility of the system has increased to a minimal amount that improves the ease of positioning the system in the subject for the treatment of the target tissue.

The phrase, "at least substantially rigid component," can refer a component that is rigid, or sufficiently rigid such that the desired function is obtained, under the forces that are created with normal use. For example, a desired function may be to prevent or inhibit the occurrence of a bending moment of the rigid component at one or more points along the length of a retractor upon expansion of the retractor in the subject. In some embodiments, the systems taught herein can have a retractor with four retractor elements, at least two of which are expandable in the subject to create a working space for a treatment. In this example, the expansion of the at least two retractor elements toward the target tissue to create the working space requires a force sufficient to retract the tissue and, creates an opposing force in the opposite direction that can create the bending moment in the rigid component. One of skill should appreciate that such a bending moment can be problematic, for example, where it contributes to an instability that affects the user's control over the position of the retractor during a treatment of the target tissue. In such embodiments, a component that prevents or inhibits the bending moment can be "at least substantially rigid," for example, where the user retains a desired level of control, or at least sufficient control, over the position of the retractor during the retraction of the target tissue. In some embodiments, a component that prevents or inhibits a bending moment, whether in or out of the subject, can be at least substantially rigid where the bending of the component due to the expansion of the retractor creates a deflection that ranges from 0.0 to about 5 degrees, about 1.0 degree to about 10 degrees, about 2.0 degrees to about 12 degrees, about 3.0 degree to about 10 degrees, about 1.0 degree to about 15 degrees, about 1.0 degree to about 9.0 degrees, about 1.0 degree to about 8.0 degrees, about 1.0 degree to about 7.0 degrees, about 1.0 degree to about 6.0 degrees, about 1.0 degree to about 5.0 degrees, about 1.0 degree to about 4.0 degrees, or any range therein in increments of about 0.1 degree. In some embodiments, the deflection of the rigid component cannot exceed about 1.0 degree, about 2.0 degrees, about 3.0 degrees, about 4.0 degrees, about 5.0 degrees, about 6.0 degrees, about 7.0 degrees, about 8.0 degrees, about 9.0 degrees, about 10.0 degrees, or any 0.1 degree increment therein. The bending can be measured, for example, as a point of deflection from the original position of the rigid component's axis from force created on the rigid component through the expansion.

The terms "substantial" or "substantially" can be used interchangeably in some embodiments, and can be described using any relative measures acceptable by one of skill. For example, relative percentages can be used to indicate a substantial amount, substantial change, substantial difference, substantial function, or the like. In some embodiments, the percentage can be greater than 10%, greater than 20%, greater than 30%, greater than 40%, or greater than 50%. In some embodiments, the percentage can be greater than 60%, greater than 70%, or greater than 80%. And, in some embodiments, the percentage can be greater than 90%, greater than 95%, or in some embodiments, even greater than 99%. For example, a substantial [amount]" or a "substantial [change]", can include any amount or change relative to a reference parameter. The amount or change, for example, can include an increase or decrease relative to the reference parameter, can be compared to a reference point for the parameter. The deviation from the reference point can be, for example, in an amount of at least 1%, at least 2%, at least 3%, at least 5%, at least 10%, at least 15%, at least 20%, at least 25%, at least 30%, at least 35%, at least 40%, at least 45%, or any 1% increment therein. Also, for example, a "substantial [function]" or "substantially [functioning]" limitation can serve as a comparison to a reference function parameter, to indicate a deviation that will still provide the intended function. Reference functions can include, for example, floating, aperistalsis, attaching, flexing, rigidity, a position or positioning relative to another object, and the like. The deviation from the reference point can be, for example, in an amount of less than 1%, less than 3%, less than 5%, less than 10%, less than 15%, less than 20%, less than 25%, less than 30%, less than 35%, less than 40%, less than 45%, or any 0.1% increment therein. For example, a component can have an acceptable, substantial [function] when it deviates from the reference by less than the acceptable deviation.

As such, the system can include a floating, multi-lumen-catheter retractor system for ease of positioning in a subject, and such systems can be designed to provide a minimally invasive treatment of the subject. In some embodiments, the systems comprise a highly flexible outer tube configured for guiding a floating channel and a floating endoscope in an at least substantially floating arrangement within the system. This flexible outer tube can have a lumen, a proximal end, and a distal end. And, during a use of the system, the floating channel can serve as a guide through which a tool is manipulated in a treatment of a target tissue in a subject. In some embodiments, the tool can include a grasper, a forcep, a scissor, a knife, a dissector, an endoscopic stapler, a tissue loop, a clip applier, a suture-delivering instrument, or an energy-based tissue coagulator or cutter. And, in some embodiments, the floating channel can have an elevator component for moving a bendable section to manipulate the tool. In some embodiments, at least one channel and/or the endoscope can have at least substantial freedom to move within the outer tube during operation, or "float," such that the system can be considered to be a floating, multi-lumen-catheter retractor system as taught herein.

Likewise, the system can also comprise a stable, yet dynamic operative environment in that it can include a reversibly-expandable retractor that expands to form a treatment space in the subject. The retractor can be configured, for example, for the expansion to occur distal to the distal end of the outer tube and at least substantially render the target tissue aperistaltic for the treatment; wherein, during a use of the system in a subject, the floating channel can be at least substantially attached to the lumen of the outer tube at a first proximal location and a first distal location, and be at least substantially floating in the lumen of the outer tube between the first proximal location and the first distal location. Likewise, during the use of the system, the floating endoscope can be at least slidably-attached to the lumen of the outer tube at a second proximal location and a second distal location, and be at least substantially floating in the lumen of the outer tube between the second proximal location and second distal location. And, during the use of the system, the at least substantially floating arrangement can at least substantially increase the flexibility of the system over a second such system, the second such system having a lumen for a tool and an endoscope affixed to the lumen throughout the length of the outer tube between the proximal end and the distal end of the outer tube. The increased flexibility of the at least substantially floating arrangement can facilitate an ease of positioning the system in the subject for the treatment of the target tissue. Moreover, the retractor can be a reversibly-stabilized and reversibly-expandable retractor, retractor forming an asymmetrical treatment space upon the expansion. And, the retractor can be configured to reversibly stiffen an otherwise flexible arrangement of the retractor, the flexible arrangement designed to facilitate the ease of positioning of the system in the subject and to reversibly stiffen for the expansion of the retractor.

Figure 2A:
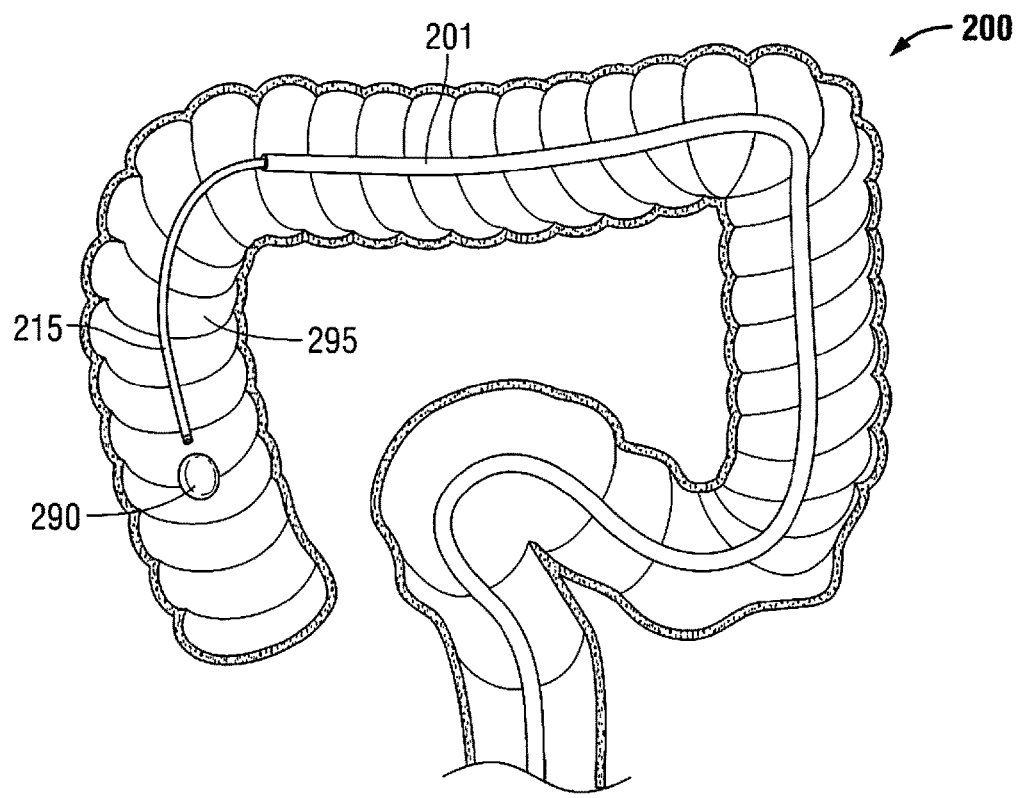
FIGS. 2A and 2B illustrate how a system as taught herein can be positioned for treating a lesion in the ascending colon, according to some embodiments.
Figure 2B:
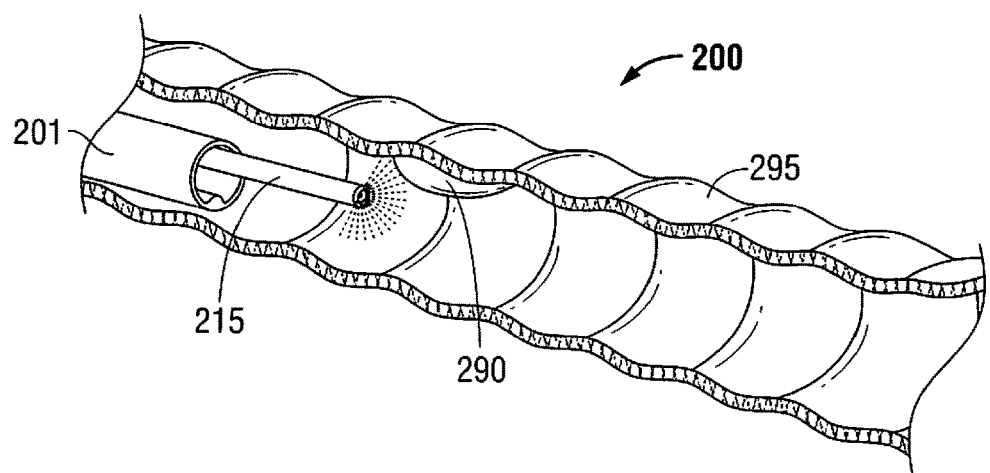

FIGS. 2A and 2B illustrate how a system as taught herein can be positioned for treating a lesion in the ascending colon, according to some embodiments. It should be appreciated that any series of steps and methods known to one of skill to be useful in the positioning 200 can be used with systems taught herein. FIG. 2A illustrates how an endoscope 215 can be used to locate the lesion, a target tissue 290 in a portion of the ascending colon 295. FIG. 2B illustrates how the multi-lumen-catheter retractor system 201 can be guided to the target tissue 290 using the endoscope 215 as a guide for the positioning 200 of the system in the treatment of the target tissue 290.

Figure 3A:
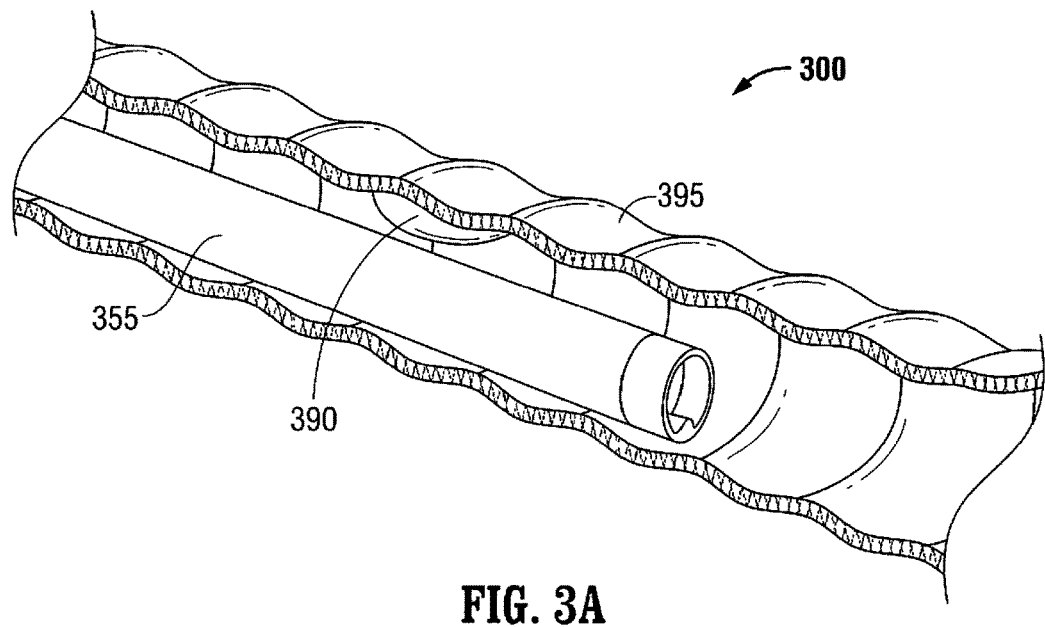
FIGS. 3A-3L illustrate how a system as taught herein can be used in removing a lesion in a colon, according to some embodiments.
Figure 3B:
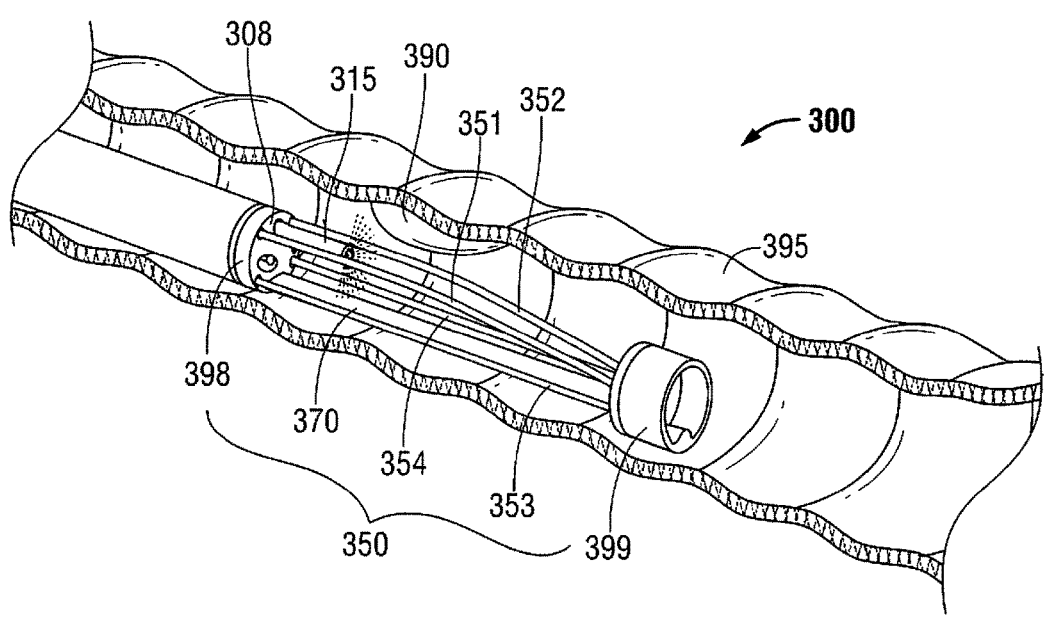

FIGS. 3A-3L illustrate how a system as taught herein can be used in removing a lesion in a colon, according to some embodiments. The system can be positioned as in FIGS. 2A and 2B in the treatment 300 of a gastrointestinal lesion 390, and a multidirectional and multi-angular approach to the lesion can be used. As in FIGS. 2A and 2B, for example, the approach can include identifying a lesion in a gastrointestinal lumen of a subject using an endoscope 315; and, forming a substantially rigid and stable endoluminal working area for treating a target tissue, the gastrointestinal lesion 390. In FIG. 3A, the system is positioned at the lesion 390, and in FIG. 3B, the expandable retractor 350 expands to create an asymmetrical working space 360.

Figure 3C:
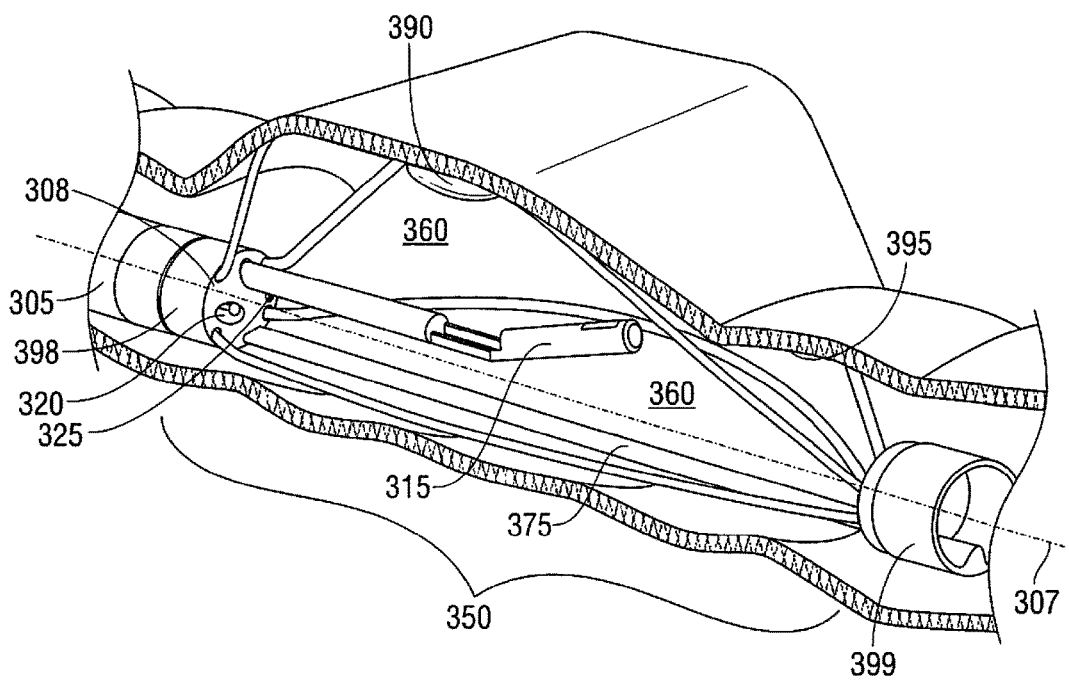
Figure 3D:
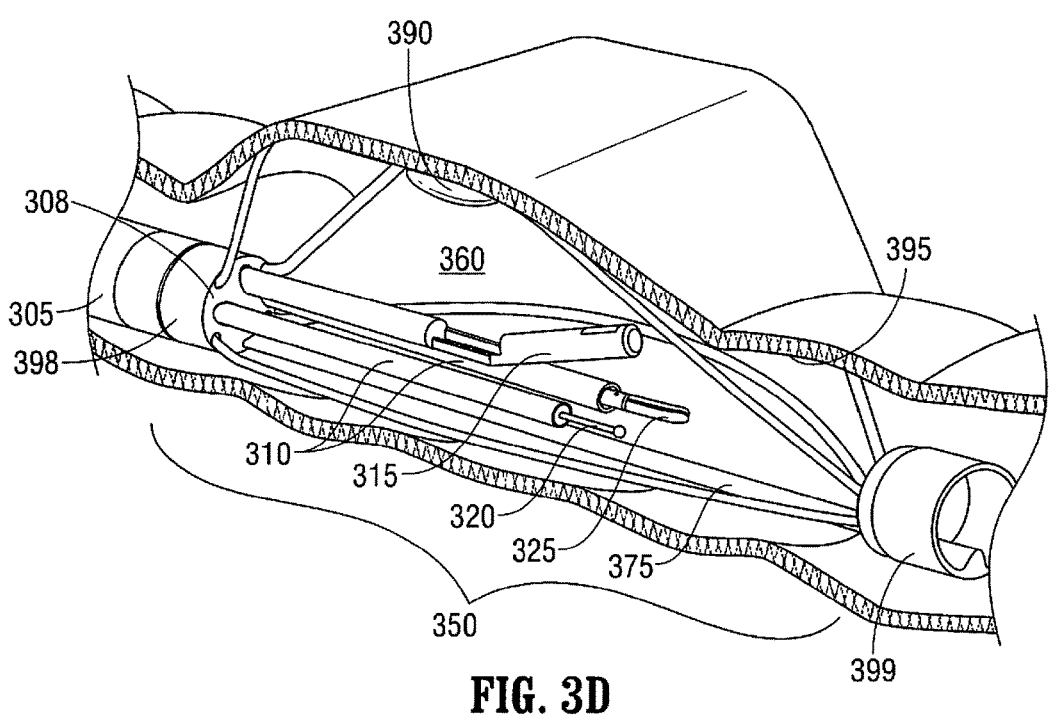

FIGS. 3C and 3D illustrate the creation of the working space 360, and manipulation of the endoscope 315 and tools 320, 325. After positioning the retractor 350 in proximity to the lesion 390, the retractor 350 is expanded to form the asymmetrical working space 360 for the treating of the lesion 390. The system can have any configuration taught herein, such as (i) at least one independently manipulable-and-articulable scope 315 to be used in viewing the lesion 390, (ii) at least one tool channel 310 for at least one independently manipulable-and-articulable tool 320, 325 to be used in the treating of the lesion 390, and (iii) the retractor 350, which can be an asymmetrically expandable structure. In some embodiments, the retractor 350 can be expanded asymmetrically toward the lesion 390, the expanding including a portion of the retractor 350 pushing on tissue surrounding the lesion 390 to increase the working area by providing an asymmetrical working area and thus facilitate an entry of the lesion 390 into the working area 360 for the treating. The retractor 350 can be located distal to the distal end of the outer tube 305 and the asymmetrical working area 360 can be substantially rigid and stable relative to the independently manipulable-and-articulable scope 315 and the at least one tool 320, 325 to facilitate treating the lesion 390. The treating of the lesion 390 can include, for example, (i) viewing the lesion 390 with the articulating scope 315 and (ii) using the at least one tool 320, 325 in the treatment of the lesion 390 with a multidirectional and multi-angular approach to the lesion 390 in the asymmetrical working area 360.

In some embodiments, the independently manipulable-and-articulable scope 315 and the at least one tool 320, 325 can be independently movable axially in the working area 360, independently rotatable in the working area 360, and independently bendable in at least one direction in the working area 360. Accordingly, in some embodiments, the portion of the retractor 350 pushing on the tissue surrounding the lesion 390 can be expanded further from the central axis 307 of the distal end of the outer tube 305 than other portions of the retractor to provide an even larger working area 360 for the treating of the lesion 390 when compared to a second such structure that merely expands symmetrically around the central axis 307 of the distal end of the outer tube 305.

Figure 3E:
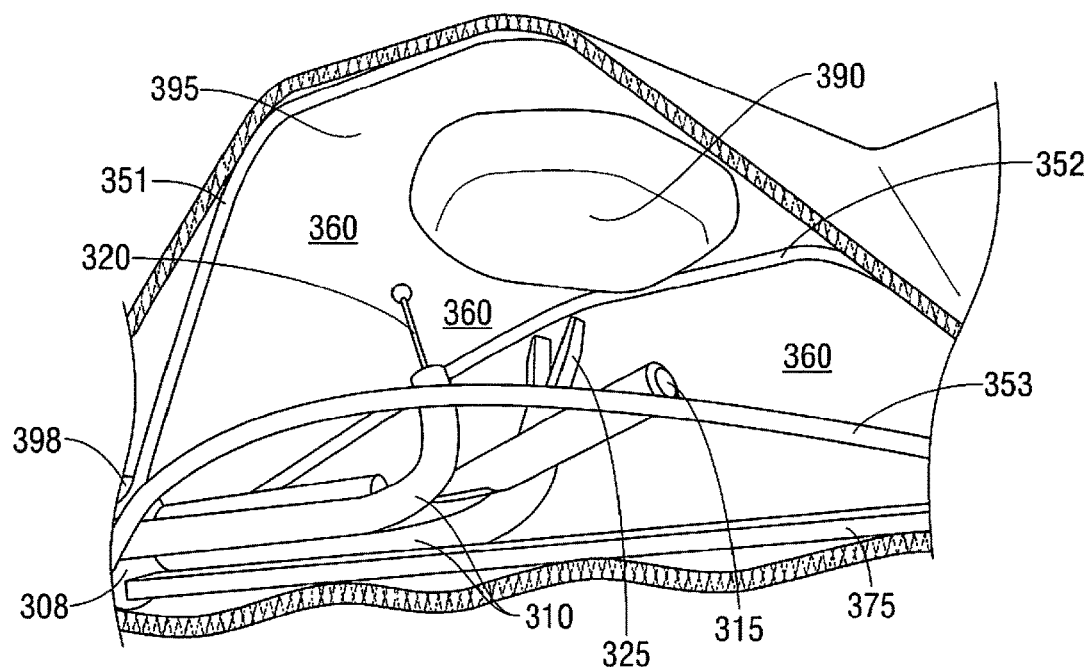
Figure 3F:
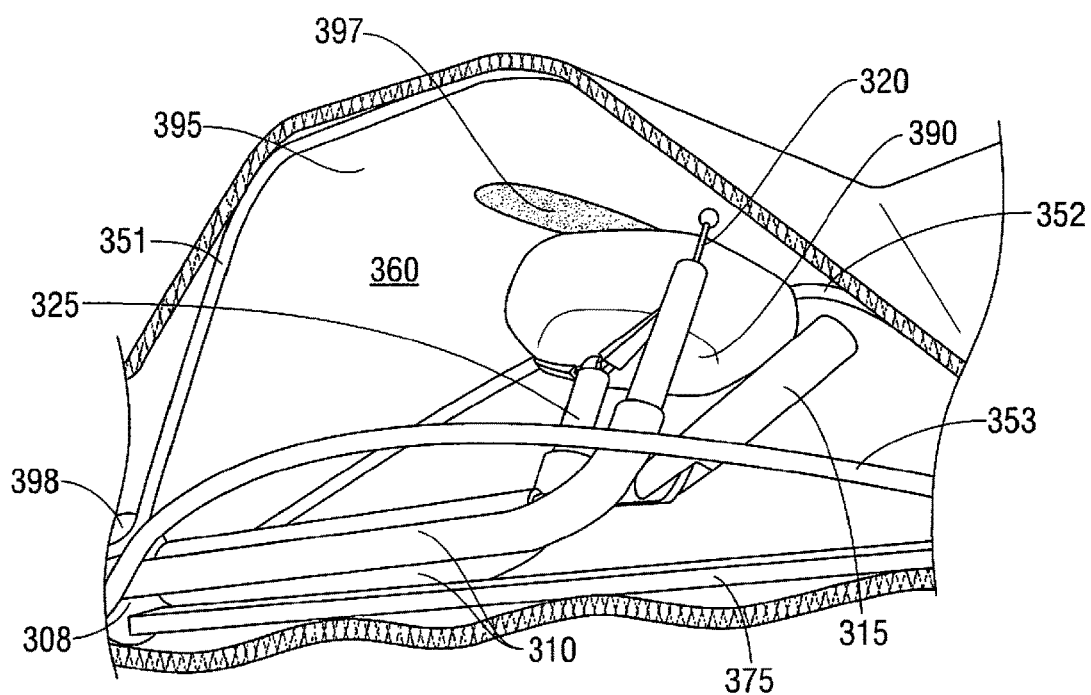
Figure 3G:
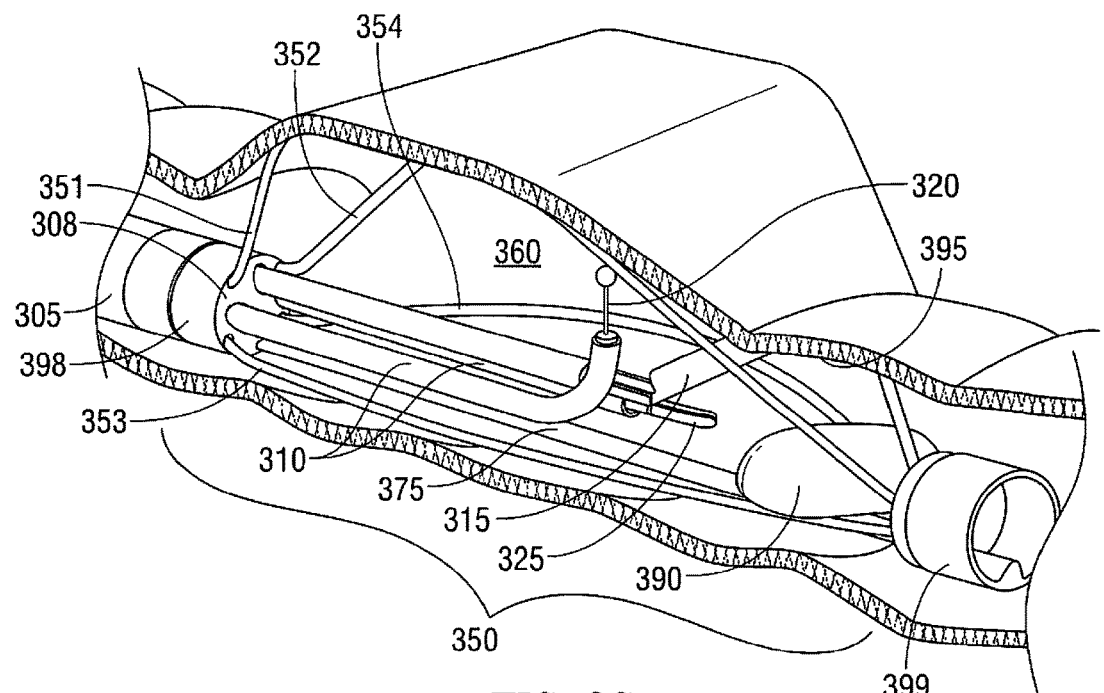
Figure 3H:
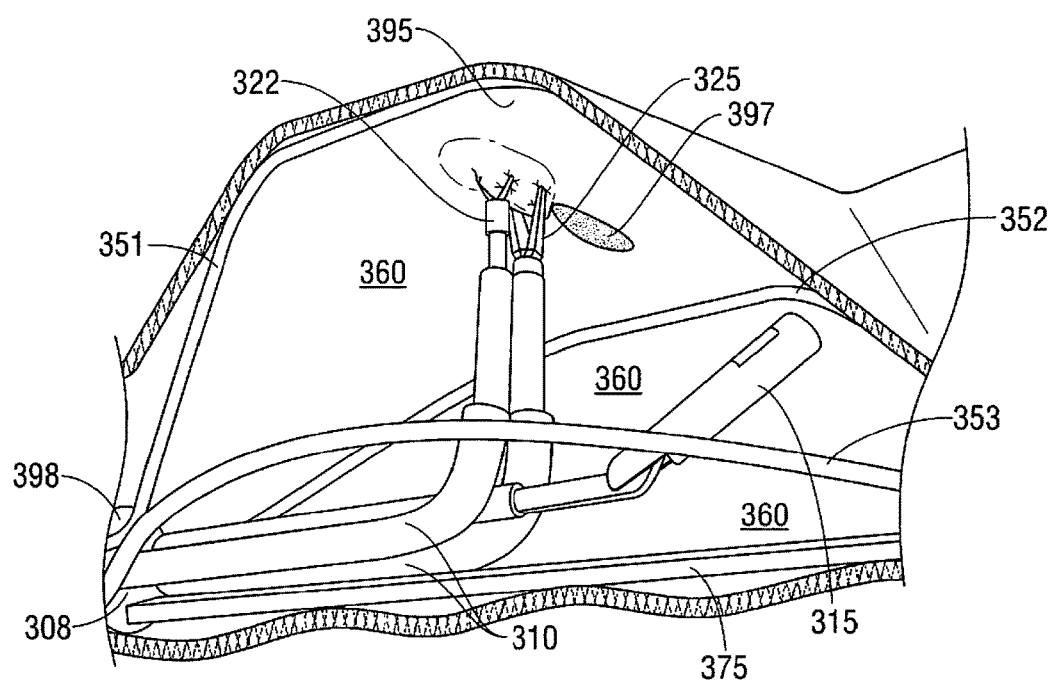
Figure 3I:
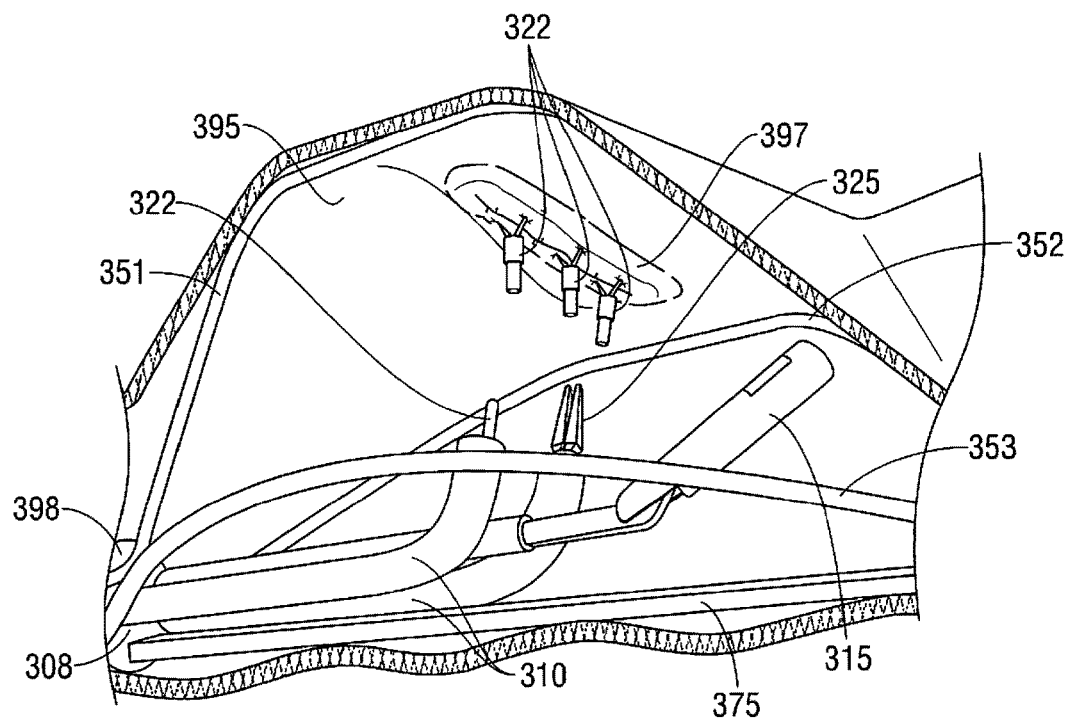
Figure 3J:
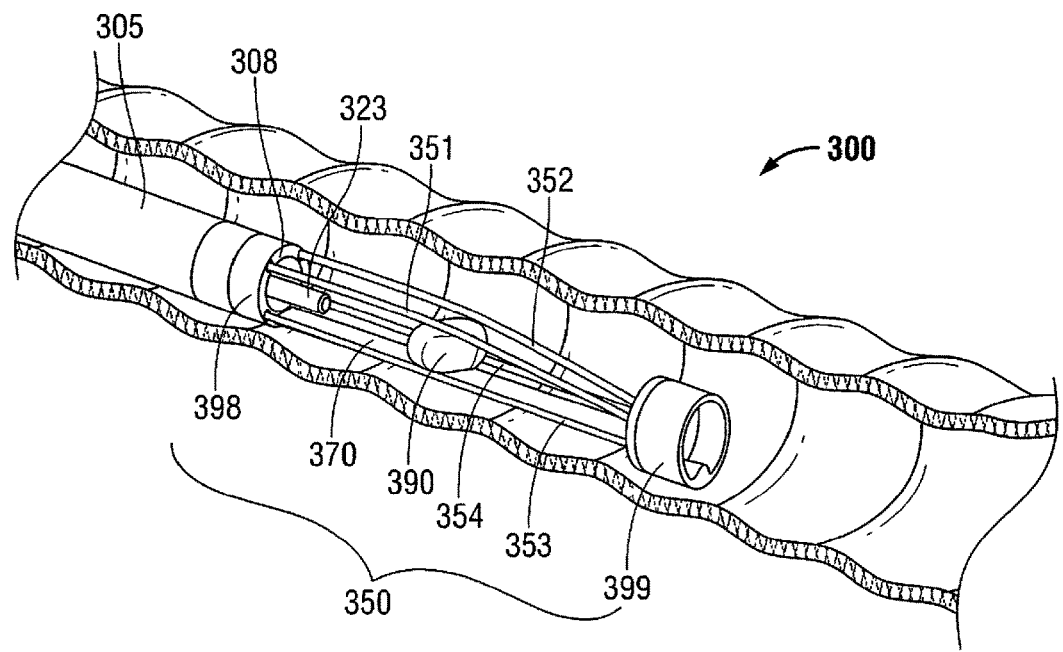
Figure 3K:
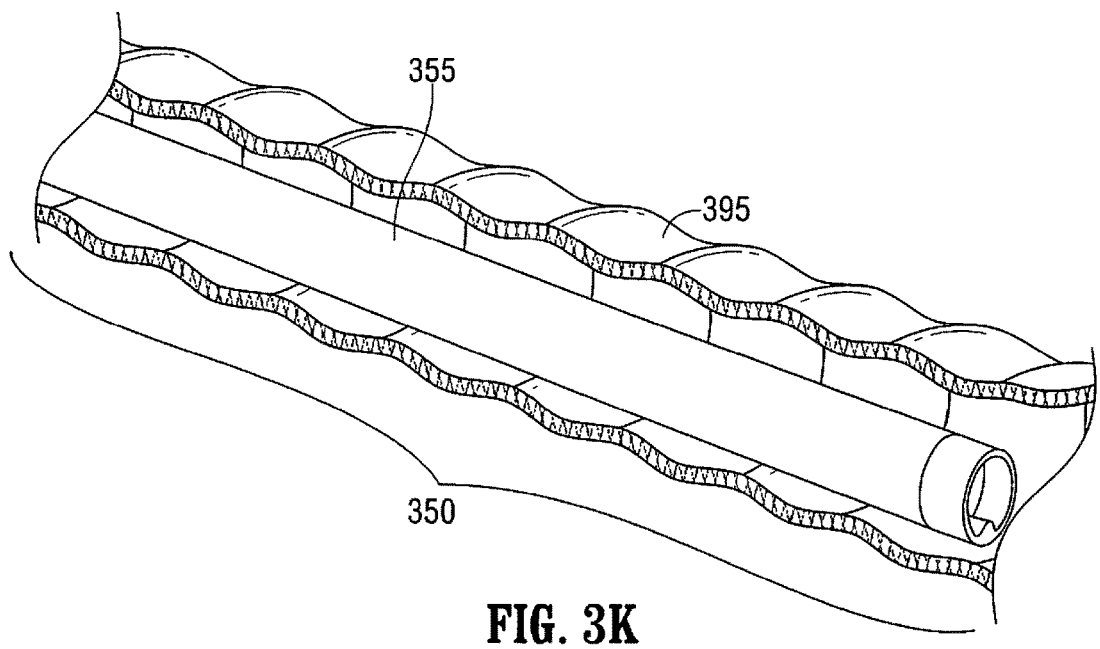
Figure 3L:
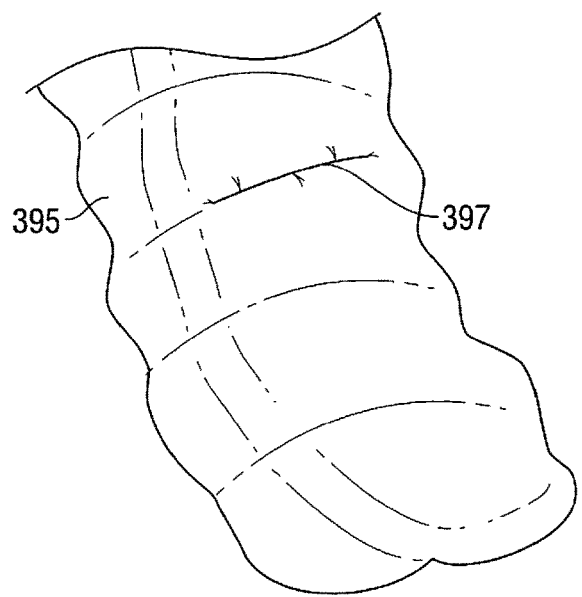

FIG. 3E illustrates a multidirectional and multi-angular approach to the lesion 390, showing the step of positioning the work area 360, endoscope 315, and tools 320, 325 in relation to the lesion 390. After the retractor 350 is expanded, the user of the system can view and approach the lesion 390 with the tools 320, 325 from nearly any desired angle within the working space 360. FIG. 3F illustrates the versatility of the system, showing the step of removing the lesion 390 using tool 320 to excise the lesion 390 from an independently chosen first angle, while tool 325 can be used to grasp the lesion 390 from an independently chosen second angle and endoscope 315 can be used to view the lesion 390 from an independently chosen third angle. After the excision of the lesion 390 from the gastrointestinal tract 395, a tissue defect 397 remains. FIG. 3G illustrates the step of releasing the excised lesion 390 into the retractor assembly in preparation for completion of the procedure. FIGS. 3H and 3I illustrate the step of closing the tissue defect 397, showing that tool 320 for excision of the lesion 390 has been replaced by tool 322 for closure of the lesion. FIGS. 3J and 3K illustrate the steps of capturing the lesion 390 for removal using tool 323 and collapsing the retractor 350 in preparation for removal of the system from the subject, including the use of an optional retractor cover 355. FIG. 3L is a view of the closed tissue defect following completion of the treatment.

In some embodiments, as shown for example in FIGS. 3B-3J, the system can comprise a stable, yet dynamic operative environment in that it can include a reversibly-expandable retractor 350 that expands to form a treatment space 360 in the subject. The retractor 350 can be configured, for example, for the expansion to occur distal to the distal end 308 of the outer tube 305. In some embodiments, the retractor can at least substantially render the target tissue 390 aperistaltic for the treatment. The retractor 350 can have a variety of configurations to serve, for example, as a scaffolding within the gastrointestinal tract 395. For example, the retractor 350 can include retractor elements 351, 352, 353, 354, along with a proximal coupler 398 operably connected to the retractor elements 351, 352, 353, 354, whether at least substantially attached and/or at least slidably-engaged to the retractor elements 351, 352, 353, 354, and a distal nexus 399 for a distal point of an operable connection with the retractor elements 351, 352, 353, 354. The distal nexus 399 is shown in the shape of a ring, although it can be virtually any shape desirable to one of skill, such as a cone, hemisphere, sphere, and the like, and it may or may not include a port for passage of the endoscope beyond the distal end of the system.

Moreover, the retractor 350 can be a reversibly-stabilized and reversibly-expandable retractor, the retractor 350 forming an asymmetrical treatment space 360 upon the expansion. And, the retractor 350 can be configured to reversibly stiffen an otherwise flexible arrangement of the retractor 350, the arrangement designed to facilitate ease of positioning of the system 300 in the subject and to reversibly stiffen for the expansion of the retractor 350. The stabilization of the retractor 350 can, in some embodiments, include a means for stabilizing the retractor 350 through a stabilizer subsystem as taught herein, the stabilizer having, for example, an at least substantially-rigid beam 375 to support the expanded retractor 350.

Figure 4A:
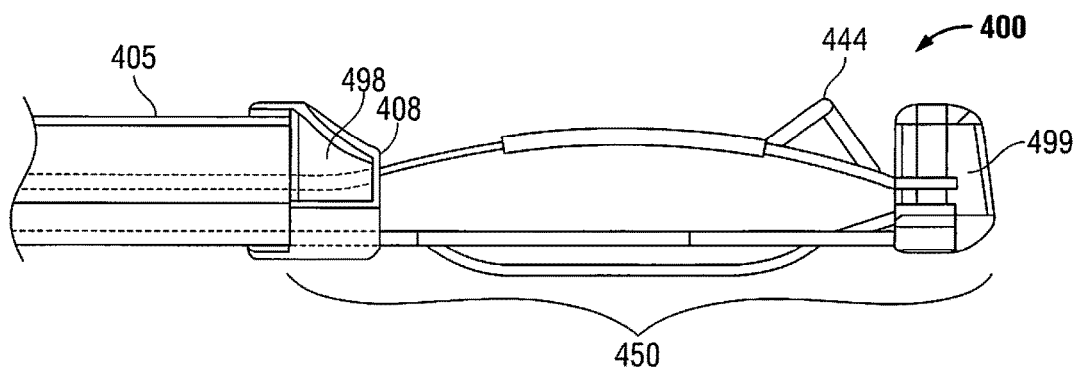
FIGS. 4A-4E illustrate details of a system as taught herein, in side, axial, and oblique views of expanded and collapsed configurations, and including a stabilizer subsystem, according to some embodiments.
Figure 4B:
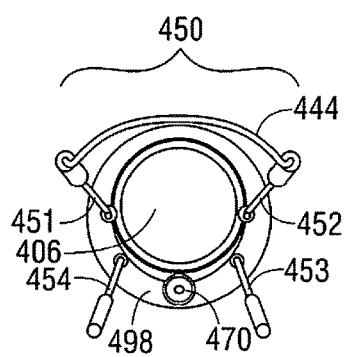
Figure 4C:
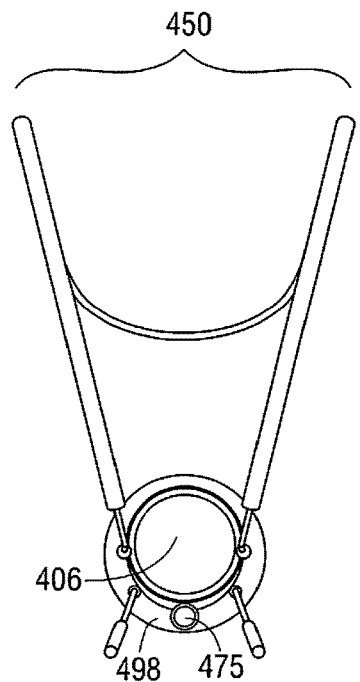

FIGS. 4A-4E illustrate details of a system as taught herein, in side, axial, and oblique views of expanded and collapsed configurations, and including a stabilizer subsystem, according to some embodiments. The figures illustrate an example of a multi-lumen catheter system having a reversibly-stabilized and reversibly-expandable retractor for a minimally invasive treatment of a subject. FIGS. 4A-4C illustrate side and axial views that show that the system 400 can comprise a flexible outer tube 405 for guiding a channel (not shown) and an endoscope (not shown) within the system 400. The flexible outer tube 405 has a lumen, a proximal end (not shown), and a distal end 408. The channel (not shown) serves as a guide through which a tool (not shown) can be manipulated in a treatment of a target tissue in a subject. In some embodiments, the retractor 450 can be a reversibly-stabilized and reversibly-expandable retractor 450 forming a treatment space upon expansion and configured for the expansion to occur distal to the distal end 408 of the outer tube 405. The retractor 450 can be designed to reversibly-stiffen an otherwise flexible arrangement of the retractor 450, the flexible arrangement designed to facilitate the positioning of the system in the subject and to reversibly-stiffen for the expansion of the retractor 450. In these embodiments, the reversibly-stiffened arrangement of the retractor 450 can form an at least substantially-rigid beam 475 from an otherwise flexible beam 470 as a structural support for the expansion of the retractor 450. In some embodiments, the stabilizer subsystem can include the flexible beam 470, which may comprise a flexible tube, and a means for creating the at least substantially-rigid beam 475. The means, as taught herein, can include all embodiments taught herein, including the mechanisms for slidably-engaging an at least substantially-rigid rod or beam, for example, within the flexible rod or beam 470 prior to expanding the retractor. In some embodiments, the terms "rod" and "beam" can be used interchangeably and, in some embodiments, the terms "beam" and "tube" can be used interchangeably.

In some embodiments, the flexible beams taught herein can comprise a polymer, such as polyimide, polyether block amides (PEBAX), nylon, polyethylene, polyurethane, polyvinylchloride (PVC), PEEK, or polytetrafluoroethylene (TEFLON). One of skill will appreciate that the flexible beams can be reinforced tubes made from components and designs known to the art. The flexible beam can be, for example, a flexible tube that is reinforced with metal wires, braids, or coils that include, for example, a metal such as a stainless steel or NITINOL. In some embodiments, the flexible tube can be kink resistant and transmit torque. And, in some embodiments, the flexible tube can comprise a combination of both flexible sections and rigid sections. In these embodiments, a flexible section can lie-between rigid sections, for example. Such flexible tubes can include composites of overlapping tubes joined using any method known to one of skill, including bonding using epoxy or cyanoacrylates, in some embodiments.

In some embodiments, any of the systems taught herein can include a bridge member to add stability to the retractor. For example, bridge member 444 is configured to maintain a desired orientation of the retractor elements 451, 452, 453, 454 during the expansion, the bridge member 444 operably stabilizing at least two 451, 452 of the four retractor elements 451, 452, 453, 454. Moreover, in some embodiments, each of the systems taught herein can have an outer tube that is wire-reinforced, such as mesh, braided, or the like, to provide kink resistance and torqueability to the system, as well as to further facilitate a positioning of the system in the subject.

Figure 4D:
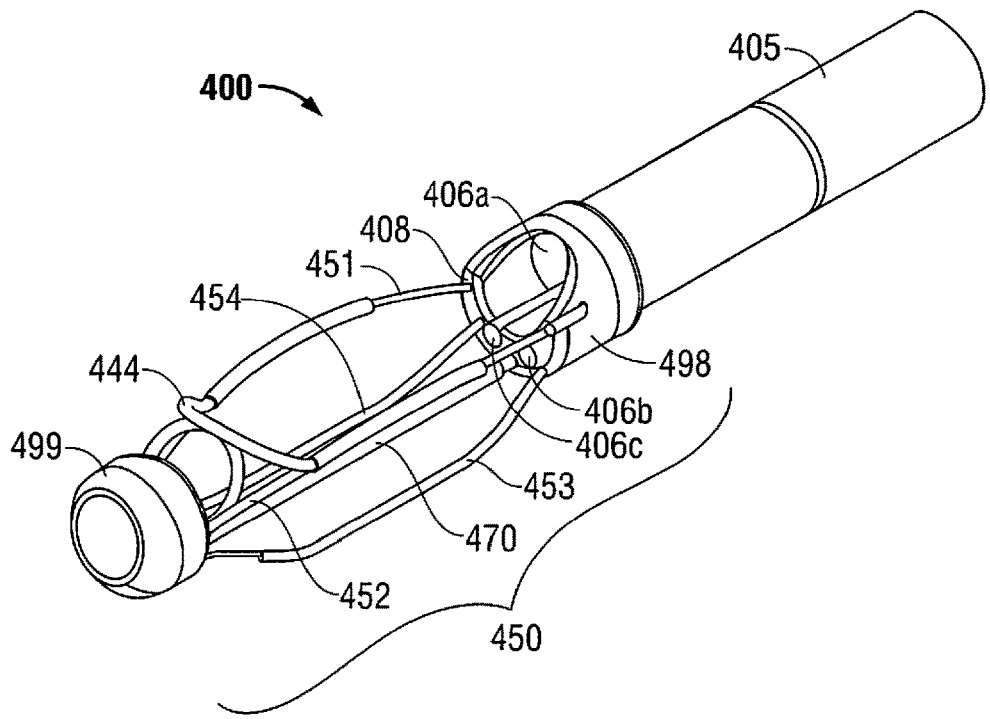
Figure 4E:
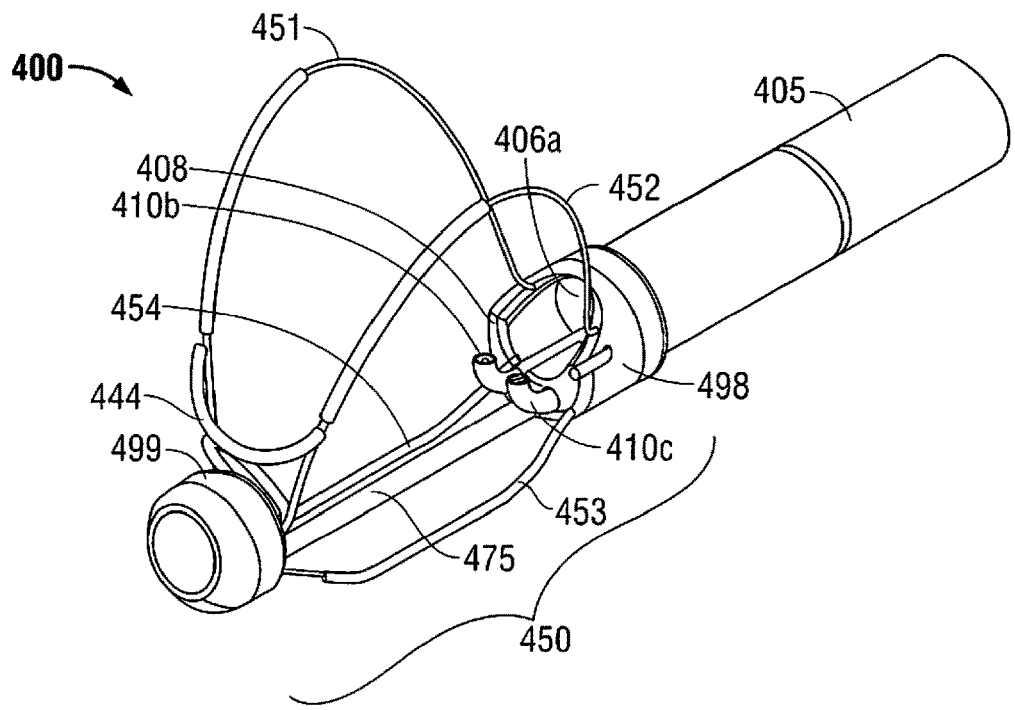

FIGS. 4D and 4E illustrate oblique views of the system 400 in collapsed and expanded configurations. The multi-lumen concept is presented with clarity in these figures, showing multiple lumens 406a, 406b, 406c in the system 400. Lumen 406a can contain an endoscope (not shown), lumen 406b can contain a first working channel 410b for a first tool (not shown), and lumen 406c can contain a second working channel 410c for a second tool (not shown). FIG. 4D in the collapsed configuration has a flexible beam 470, whereas FIG. 4E in the expanded configuration has a rigid beam 475 that was formed from the flexible beam. A rigid beam can be formed from a flexible beam, in some embodiments, by slidably inserting a rigid rod into a flexible tube that composes the flexible beam. In many embodiments, the term "tool channel" can be used interchangeably with the term "working channel." And, in some embodiments, a channel can be a separate component placed inside the outer tube, or it can be a space remaining in the lumen of the outer tube between separate components that were placed in the outer tube, the separate components including, for example, an endoscope, a working channel, an instrument, a guide, and the like.

In some embodiments, as shown for example in FIGS. 4A-4E, the system can comprise a stable, yet dynamic operative environment in that it can include a reversibly-expandable retractor 450 that expands to form a treatment space 460 in the subject. The retractor 450 can be configured, for example, for the expansion to occur distal to the distal end 408 of the outer tube 405. In some embodiments, the retractor can at least substantially render the target tissue 490 aperistaltic for the treatment. The retractor 450 can have a variety of configurations to serve, for example, as a scaffolding within the gastrointestinal tract 495. For example, the retractor 450 can include retractor elements 451, 452, 453, 454, along with a proximal coupler 498 operably connected to the retractor elements 451, 452, 453, 454, whether at least substantially attached and/or at least slidably-engaged to the retractor elements 451, 452, 453, 454, and a distal nexus 499 for a distal point of an operable connection with the retractor elements 451, 452, 453, 454.

Moreover, the retractor 450 can be a reversibly-stabilized and reversibly-expandable retractor, the retractor 450 forming an asymmetrical treatment space 460 upon the expansion. And, the retractor 450 can be configured to reversibly stiffen an otherwise flexible arrangement of the retractor 450, the arrangement designed to facilitate ease of positioning of the system 400 in the subject and to reversibly stiffen for the expansion of the retractor 450. The stabilization of the retractor 450 can, in some embodiments, include a means for stabilizing the retractor 450 through a stabilizer subsystem as taught herein, the stabilizer having, for example, an at least substantially-rigid beam 475 to support the expanded retractor 450.

Figure 5A:
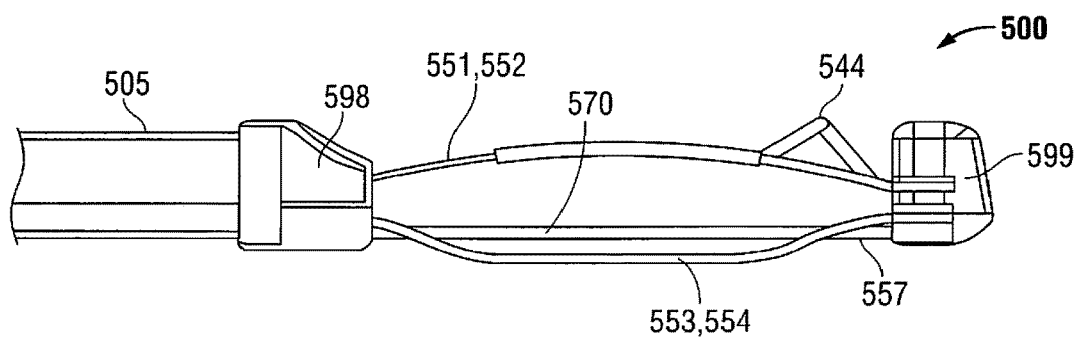
FIGS. 5A-5D illustrate side and top views of a system as taught herein, having side views and top views of expanded and collapsed configurations, according to some embodiments.
Figure 5B:
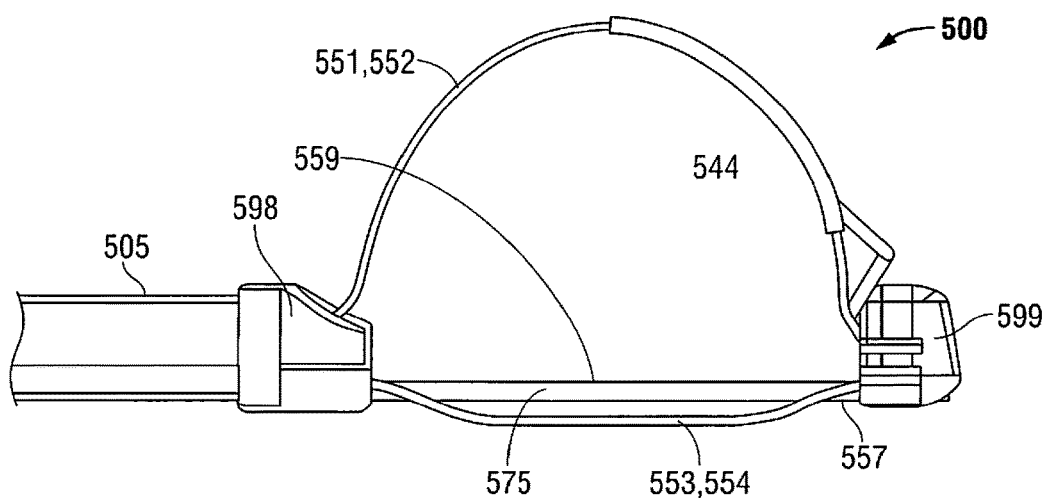
Figure 5C:
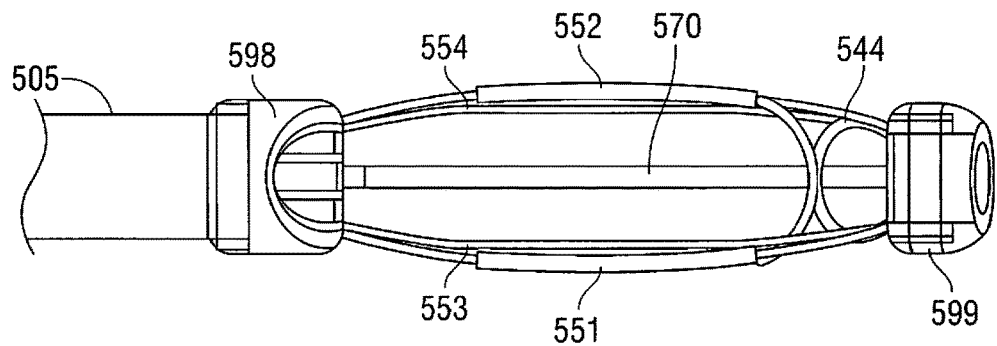
Figure 5D:
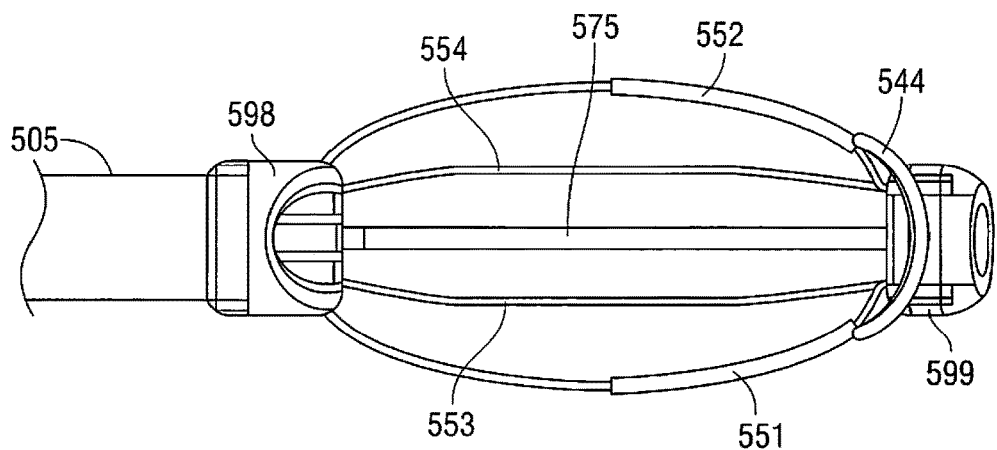

FIGS. 5A-5D illustrate side and top views of a system as taught herein, having side views and top views of expanded and collapsed configurations, according to some embodiments. FIGS. 5A and 5B illustrates side views of system 500 in collapsed and expanded configurations showing an example of an asymmetric work space that can be formed during an endoscopic procedure using the system 500. And, as shown in FIG. 5B, the expansion can occur in a disproportionally greater amount on the luminal side 559 of the rigid beam 575 than the abluminal side 557 of the rigid beam 575 to increase the treatment, or working, space 560, the treatment space 560 having a volume that is asymmetrically distributed around the rigid beam 575. In some embodiments, the expansion can occur in an amount that is at least 5× greater on the luminal side 559 of the rigid beam 575 than the abluminal side 557 of the rigid beam 575. And in some embodiments, the expansion can be at least 1.1× greater, at least 1.3× greater, at least 1.5× greater, at least 2.0× greater, at least 2.5× greater, at least 3.0× greater, at least 3.5× greater, at least 4.0× greater, at least 4.5× greater, at least 5.0× greater, at least 5.5× greater, at least 6.0× greater, at least 6.5× greater, at least 7.0× greater, at least 7.5× greater, at least 8.0× greater, at least 8.5× greater, at least 9.0× greater, at least 9.5× greater, at least 10.0× greater, or any 0.1× increment within this range, on the luminal side of the beam than the abluminal side of the beam.

In some embodiments, as shown for example in FIGS. 5A-5D, the system can comprise a stable, yet dynamic operative environment in that it can include a reversibly-expandable retractor 550 that expands to form a treatment space 560 in the subject. The retractor 550 can be configured, for example, for the expansion to occur distal to the distal end 508 of the outer tube 505. In some embodiments, the retractor can at least substantially render the target tissue 590 aperistaltic for the treatment. The retractor 550 can have a variety of configurations to serve, for example, as a scaffolding within the gastrointestinal tract 595. For example, the retractor 550 can include retractor elements 551, 552, 553, 554, along with a proximal coupler 598 operably connected to the retractor elements 551, 552, 553, 554, whether at least substantially attached and/or at least slidably-engaged to the retractor elements 551, 552, 553, 554, and a distal nexus 599 for a distal point of an operable connection with the retractor elements 551, 552, 553, 554.

Moreover, the retractor 550 can be a reversibly-stabilized and reversibly-expandable retractor, the retractor 550 forming an asymmetrical treatment space 560 upon the expansion. And, the retractor 550 can be configured to reversibly stiffen an otherwise flexible arrangement of the retractor 550, the arrangement designed to facilitate ease of positioning of the system 500 in the subject and to reversibly stiffen for the expansion of the retractor 550. The stabilization of the retractor 550 can, in some embodiments, include a means for stabilizing the retractor 550 through a stabilizer subsystem as taught herein, the stabilizer having, for example, an at least substantially-rigid beam 575 to support the expanded retractor 550.

Figure 6A:
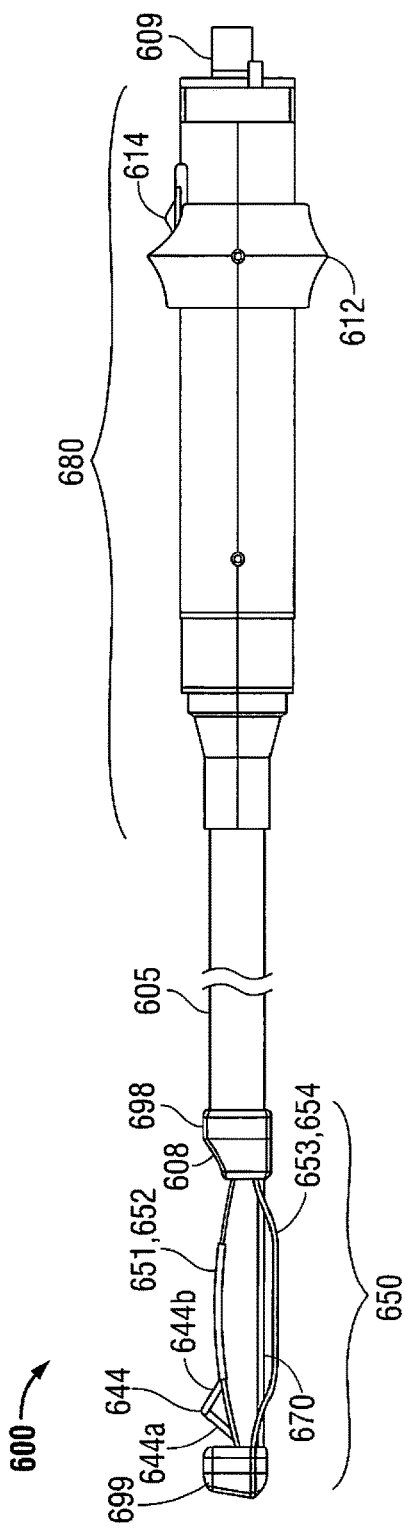
FIGS. 6A-6D illustrate side views of a system as taught herein, having side views and cross-sections of expanded and collapsed configurations of the system, according to some embodiments.
Figure 6B:
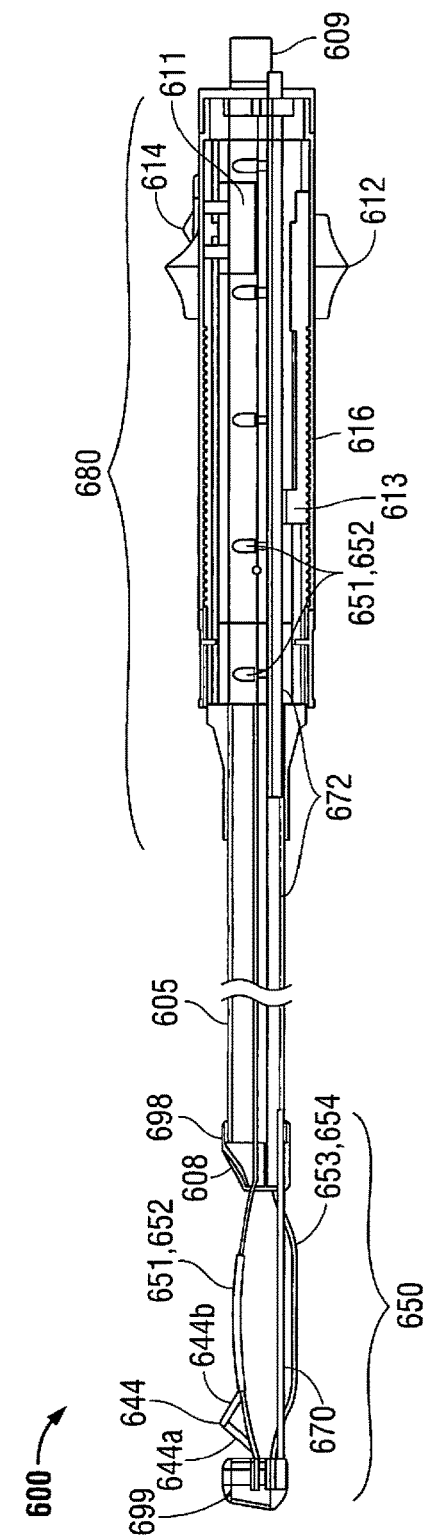
Figure 6C:
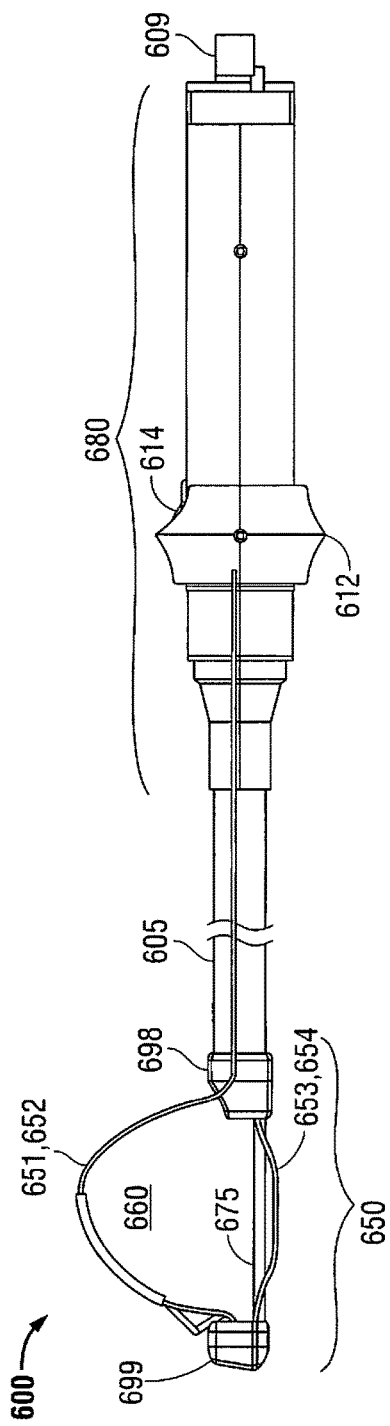

FIGS. 6A-6D illustrate side views of a system as taught herein having side views and cross-sections of expanded and collapsed configurations of the system, according to some embodiments. The figures illustrate an example of a multi-lumen catheter system having a reversibly-stabilized and reversibly-expandable retractor for a minimally invasive treatment of a subject. FIGS. 6A and 6B illustrates a side view that shows that the system 600 can comprise a flexible outer tube 605 for guiding a channel (not shown) and an endoscope (not shown) within the system 600. The flexible outer tube 605 has a lumen, a proximal end (not shown), and a distal end 608. The channel (not shown) serves as a guide through which a tool (not shown) can be manipulated in a treatment of a target tissue in a subject. In some embodiments, the retractor 650 can be a reversibly-stabilized and reversibly-expandable retractor 650 forming a treatment space 660 upon expansion and configured for the expansion to occur distal to the distal end 608 of the outer tube 605. The retractor 650 can be designed to reversibly-stiffen an otherwise flexible arrangement of the retractor 650, the flexible arrangement designed to facilitate the positioning of the system in the subject and to reversibly-stiffen for the expansion of the retractor 650. In these embodiments, the reversibly-stiffened arrangement of the retractor 650 can form an at least substantially-rigid beam 675 from an otherwise flexible beam 670 as a structural support for the expansion of the retractor 650.

Handle 680 includes entry ports for operatively combining the system with external components, such as an entry port 609 for an endoscope (not shown) and/or a tool (not shown). The handle is also operatively connected to the proximal end of the outer tube 605 and can have exit ports from the handle 680 into the outer tube 605. The system can include a stabilizer subsystem, in some embodiments. For example, a stabilizer actuator 612 can be included on the handle 680 to reversibly-stiffen the flexible beam 670 to create the at least substantially-rigid beam 675 for the expansion of the retractor 650. A retractor actuator 614 can be included on the handle 680 to reversibly expand the retractor 650.

Figure 6D:
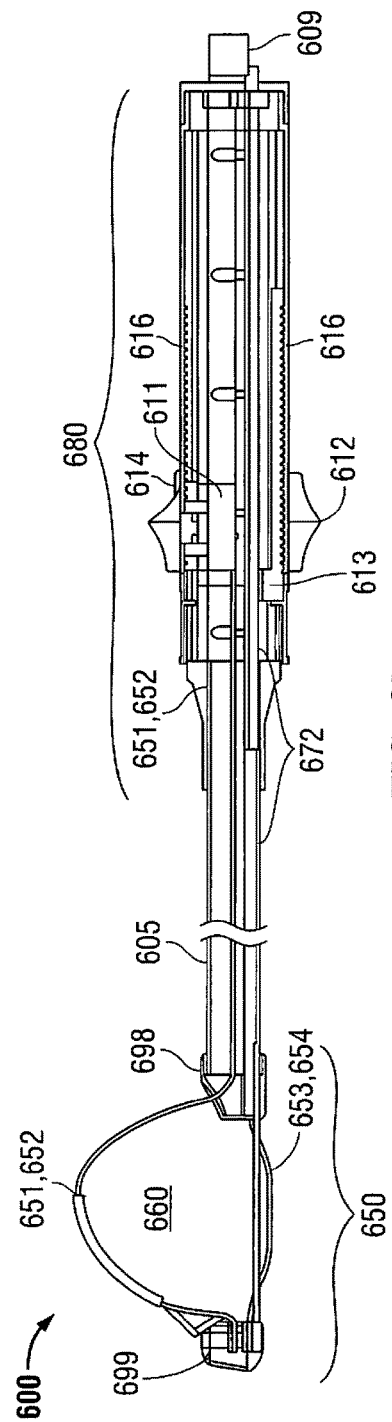

FIGS. 6D and 6E illustrate oblique views of the system 600 in expanded configurations. The expanded configurations have a rigid beam 675 that was formed from the flexible beam that is typically present in the collapsed state for positioning in the subject. The rigid beam 675 can be formed from a flexible beam, in some embodiments, by slidably inserting a rigid rod into a flexible tube that composes the flexible beam. As shown in FIGS. 6B and 6D, the stabilizer actuator 612 is operably connected to the rigid rod 672 through a rod coupler 613. Likewise, the retractor actuator 614 is operably connected to a retractor element 651, 652 through an element coupler 611. The stabilizer actuator 612 and/or the retractor actuator 614 can be reversibly engageable with the handle 680, in some embodiments, such that the stabilizer actuator 612 and/or the retractor actuator 614 can be reversibly-fixed in position relative to the handle 680. In some embodiments, the stabilizer actuator 612 and/or the retractor actuator 614 can be multi-positional, having at least three positions for expansion and/or collapse of the retractor. In some embodiments, the stabilizer actuator 612 and/or the retractor actuator 614 can have a plurality of ratchet teeth 616 to provide a plurality of positions for reversibly-fixing the retractor in position during expansion or collapse of the retractor.

One of skill will appreciate that the handle can be any of a variety of shapes to provide a desired or ergonomic position for operation of the system. By way of example, the retractor actuator can be configured as a finger-activated button on the handle 680 that slides back and forth through a slot in the handle 680 to expand or collapse the retractor elements. A means for dynamically adjusting or ratcheting the retractor position can be provided along the handle slot to lock the position of the retractor elements in place when the retractor actuator button is not pressed. A button on the opposite side of the handle can be operatively connected to the stabilizer subsystem to convert the flexible beam into a rigid beam, or convert the rigid beam into a flexible beam. The handle can have inner channels routed axially, for example, within the body of the handle and in communication with ports for tools and endoscope introduction into the outer tube. In some embodiments, the handle can be configured to require that the stabilizer actuator is activated before the retractor actuator can be activated, serving as a "safety" mechanism in the operation of the system.

As such, in some embodiments, as shown for example in FIGS. 6A-6D, the system can comprise a stable, yet dynamic operative environment in that it can include a reversibly-expandable retractor 650 that expands to form a treatment space 660 in the subject. The retractor 650 can be configured, for example, for the expansion to occur distal to the distal end 608 of the outer tube 605. In some embodiments, the retractor can at least substantially render the target tissue 690 aperistaltic for the treatment. The retractor 650 can have a variety of configurations to serve, for example, as a scaffolding within the gastrointestinal tract 695. For example, the retractor 650 can include retractor elements 651, 652, 653, 654, along with a proximal coupler 698 operably connected to the retractor elements 651, 652, 653, 654, whether at least substantially attached and/or at least slidably-engaged to the retractor elements 651, 652, 653, 654, and a distal nexus 699 for a distal point of an operable connection with the retractor elements 651, 652, 653, 654.

Moreover, as described herein, the retractor 650 can be a reversibly-stabilized and reversibly-expandable retractor, the retractor 650 forming an asymmetrical treatment space 660 upon the expansion. And, the retractor 650 can be configured to reversibly stiffen an otherwise flexible arrangement of the retractor 650, the arrangement designed to facilitate ease of positioning of the system 600 in the subject and to reversibly stiffen for the expansion of the retractor 650. The stabilization of the retractor 650 can, in some embodiments, include a means for stabilizing the retractor 650 through a stabilizer subsystem as taught herein, the stabilizer having, for example, an at least substantially-rigid beam 675 to support the expanded retractor 650.

The rigid rod can be a straight component comprising a rigid material, for example stainless steel or another metal or alloy, that is slide-able in and out of the inner diameter of the flexible tube. As such, the stabilizer subsystem can have a flexible beam or rigid beam by sliding the rigid rod proximal (i.e., anally) to the flexible tube by pulling back on the rigid rod through a mechanism operably connected to the handle. The rigid rod can be pushed forward (i.e., orally) into the flexible tube to stiffen and straighten the flexible tube. By pushing the rigid rod across the length of the flexible tube, the flexible tube, or flexible beam, becomes rigid and straight, and in effect renders the whole retractor structure at least substantially rigid and straight. One of skill in the art will appreciate that any mechanism of reversibly stiffening a flexible component in vivo may be used in some embodiments. For example, the flexible tube, or flexible beam, may also comprise a series of rigid tubes having a flexible, non-stretchable cable passing through the lumens of the tubes. When the cable is relaxed, the series of rigid tubes can be separated using, for example, a compressible component such as a spring between each of the series of rigid tubes to provide a flexible non-overlapping configuration. When the cable is tensioned, the compressible components compress, and the rigid tubes overlap, converting the flexible beam into a rigid beam.

The reversibly-stabilized retractor, as described herein, is useful in positioning the working space at the site of treatment of the target tissue as it can be rendered flexible for positioning and later rendered rigid for expansion of the retractor. During introduction of a system taught herein into a tortuous body lumen, for example a colon, the retractor can be unexpanded and flexible. This flexibility allows the retractor to bend to conform to the bends in the tortuous body lumen, so that it can be advanced with ease and not cause trauma to the lumen. The rings which hold the retractor elements together can also have lumens that allow passage of a guide such as an endoscope. In such embodiments, when the retractor is in the flexible mode for introduction, for example, the rings can be free to slide over the guide as the system is advanced forward. In some embodiments, the lumens of the rings can be large enough relative to the diameter of the guide to allow for tilting and translation of the system on the guide, helping the system conform to the bends of the guide during advancement of the system orally or anally. Once the retractor is advanced to the target location in the lumen, the flexible beam of the retractor can be straightened and stiffened as described herein. Since the system can be flexible and torsionally stiff, the proximal shaft or the handle can be easily rotated as desired relative to the location of the target lesion.

The retractor elements can have at least one pair that is pre-shaped having peaks pointing outwards at a desired angle. In some embodiments, the angle can range from about 45 degrees to about 135 degrees, about 60 degrees to about 120 degrees from each other on one side of the rigid beam, the vertex of the angle being the central axis of the rigid beam, as can be seen in the figures provided herein. In some embodiments, the angle is about 90 degrees between retractor elements. Upon expansion, the retractor elements bulge outwards on one side disproportionally more than the other retractor elements, resulting in an asymmetrical expansion of the retractor. The at least substantially rigid beam prevents or inhibits deformation of the retractor during creation of forces on the retractor in the expansion. The forces include forces from expanding tissue outwards asymmetrically, as well as the initial forces applied on the retractor elements to create an asymmetrical working space.

In some embodiments, the target lesion can be located on the side of the most expanded retractor elements so to facilitate maximizing or increasing the distance between the lesion to be treated and the portals at which the endoscope and tools are introduced into the working space. The endoscope and tools can be maneuvered independently, for example, to access the lesion at a greater range of angles than is currently clinically obtainable using state-of-the-art systems. This increased maneuverability can improve the view of the lesion and ability to manipulate and dissect the lesion. For example, a grasper can be advanced out of the instrument channel into the working space and flexed towards the polyp, grasp the polyp and retract the tissue to expose the base of the polyp for dissection by a dissection tool through the multi-channel systems taught herein. Sometimes, it can also be desired to reduce the distance between the lesion to be treated and the portals at which the endoscope and tools are introduced into the working space. For example, it can be desired to locate the lesion on the side of the least expanded retractor elements to better align the lesion with the endoscope channel substantially parallel to the lumen wall. Such a configuration may be clinically optimal while the polyp is retracted by a grasper towards the most expanded side. In such embodiments, a dissection tool can be advanced through a channel at the base of the polyp and dissect the polyp's base where it attaches to the lumen wall, while the position of the endoscope provides a close view of the base of the polyp to help identify the desired margin for dissection.

In some embodiments, any of the systems taught herein can include a bridge member, which provides structural support to add stability to the retractor. The bridge member can include any configuration conceivable by one of skill to provide additional support, such as a scaffolding means, for enhancing or buttressing the stability and rigidity of the expanded contractor. For example, bridge member 644 is configured to maintain a desired orientation of the retractor elements 651, 652, 653, 654 during the expansion, the bridge member 644 operably stabilizing at least two 651, 652 of the four retractor elements 651, 652, 653, 654. Moreover, in some embodiments, each of the systems taught herein can have an outer tube, for example outer tube 605, that is wire-reinforced, such as mesh, braided, or the like, to provide kink resistance and torqueability to the system, as well as to further facilitate a positioning of the system in the subject. In some embodiments, the bridge member 644 can be configured to reduce drag from surrounding tissue during use. For example, as shown in FIGS. 6A and 6B, the bridge member 644 can be configured to facilitate a movement of the system in a gastrointestinal tract by designing the bridge member 644 to include a forward component 644a that is inclined to facilitate forward movement orally, and a reverse component 644b that is inclined to facilitate reverse movement anally.

The bridge member can be connected to the retractor elements, for example, to maintain a desired orientation of the retractor elements as they expand against a gastrointestinal tissue, for example. As the retractor is expanded, the bridge member is also expanded outward. In some embodiments, the bridge member is operably connected only to the retractor elements that expand the most, for example the retractor elements 751, 752 in FIG. 7, which can be the members that incur the most induced forces on the retractor due to the disproportionate pressure applied to create the asymmetrical working space in the expansion. In some embodiments, the bridge can be designed to flex to prevent the retractor elements from collapsing towards each other or bending away from each other, while also providing some spring or elasticity to the system to comply gently with the tissue. One of skill will appreciate that the bridge can comprise any suitable material that provides the material characteristics desired. For example, the bridge can be formed from a curved nitinol wire in some embodiments. The ends of the nitinol wires can be connected to the retractor elements using any manufacturing process deemed suitable by one of skill for the in vivo uses taught herein, such process including, for example, tubing connectors, adhesives, or solder.

Figure 7:
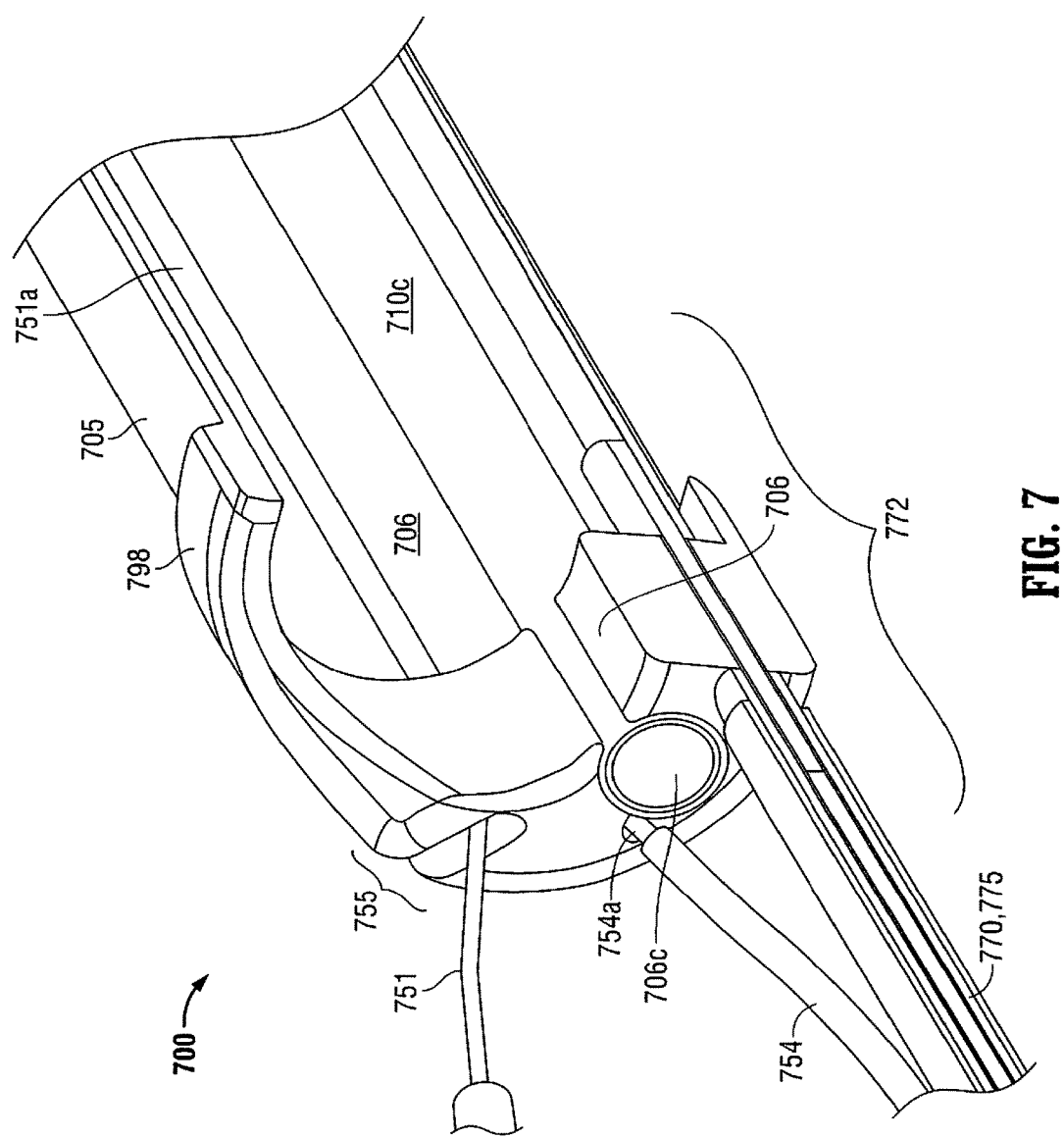
FIG. 7 illustrates a cutaway view of the distal end of the outer tube of a system as taught herein, showing components of the expansion and collapse of the retractor, according to some embodiments.

FIG. 7 illustrates a cutaway view of the distal end of the outer tube of a system as taught herein, showing components of the expansion and collapse of the retractor, according to some embodiments. The figure illustrates the distal end 708 of outer tube 705. The distal end 708 includes a slot guide 755 to control the orientation of an expanding retractor element 751, as well as a port 754a for operably receiving/supporting a lower retractor element 754. Likewise, a lumen 706c can be provided to contain a working channel 710c. The lumen 706 of the outer tube 705 can also be used to guide an endoscope (not shown) through port 706a. Only a portion 751, 754, 770, 772, 775 of the retractor components is shown to partially describe the relation between the outer tube 705 and the retractor in some embodiments. The retractor can be configured, for example, for the expansion to occur distal to the distal end 708 of the outer tube 705. For example, the retractor can include retractor elements 751, 752 (not shown), 753 (not shown), 754, along with a proximal coupler 798 operably connected to the retractor elements 751, 752 (not shown), 753 (not shown), 754, whether at least substantially attached and/or at least slidably-engaged to the retractor elements 751, 752 (not shown), 753 (not shown), 754. The retractor can be configured to reversibly stiffen an otherwise flexible arrangement of the retractor, the arrangement designed to facilitate ease of positioning of the system 700 in a subject and to reversibly stiffen for the expansion of the retractor in the subject. The stabilization of the retractor can, in some embodiments, include a means for stabilizing the retractor through a stabilizer subsystem as taught herein, the stabilizer having, for example, a flexible beam 770 that can be converted to an at least substantially-rigid beam 775, using a means for slidably engaging a rigid, or substantially rigid, component 772 as taught herein in operable connection with the flexible beam 770, to support the expanded retractor.

FIG. 8 illustrates the cutaway view of FIG. 7, showing the distal end of the outer tube of a system as taught herein, in which components of the system can be floating in the outer tube to enhance flexibility for positioning the system in a subject, according to some embodiments. The figure illustrates the distal end 808 of outer tube 805. The distal end 808 includes a slot guide 855 to control the orientation of an expanding retractor element 851, as well as a lower retractor element 854. Likewise, a lumen 806c can be provided to contain a working channel 810c. The lumen 806 of the outer tube 805 can also be used to guide an endoscope 815. Only a portion 851, 854, 870, 872, 875 of the retractor components is shown to partially describe an embodiment of the relation between the outer tube 805 and the retractor. The retractor can be configured, for example, for the expansion to occur distal to the distal end 808 of the outer tube 805. For example, the retractor can include retractor elements 851, 852 (not shown), 853 (not shown), 854, along with a proximal coupler 898 operably connected to the retractor elements 851, 852 (not shown), 853 (not shown), 854, whether at least substantially attached and/or at least slidably-engaged to the retractor elements 851, 852 (not shown), 853 (not shown), 854. The retractor can be configured to reversibly stiffen an otherwise flexible arrangement of the retractor, the arrangement designed to facilitate ease of positioning of the system 800 in a subject and to reversibly stiffen for the expansion of the retractor in the subject. The stabilization of the retractor can, in some embodiments, include a means for stabilizing the retractor through a stabilizer subsystem as taught herein, the stabilizer having, for example, a flexible beam 870 that can be converted to an at least substantially-rigid beam 875, using a means for slidably engaging a rigid, or substantially rigid, component 872 as taught herein in operable connection with the flexible beam 870, to support the expanded retractor.

During a use of the system 800, the working channel 810c can be a floating channel that is (i) at least substantially attached to the lumen of the outer tube at a first proximal location (not shown) and a first distal location 806c and (ii) at least substantially floating in the lumen 806 of the outer tube 805 between the first proximal location (not shown) and the first distal location 806c. Likewise, during the use of the system 800, the endoscope 815 can be a floating endoscope 815 that is (iii) at least slidably-attached to the lumen 806 of the outer tube 805 at a second proximal location (not shown) and a second distal location 806a and (iv) at least substantially floating in the lumen 806 of the outer tube 805 between the second proximal location (not shown) and second distal location (806a). And, during the use of the system 800, the working channel 810c and the endoscope 815 also form separate floating components of a floating arrangement that (v) at least substantially increases the flexibility of the system 800 over a second such system having separate lumens for a tool and an endoscope, the separate lumens affixed to the lumen throughout the length of the outer tube between the proximal end and the distal end of the outer tube, the increased flexibility facilitating an ease of positioning the system 800 in the subject for the treatment of the target tissue. In some embodiments, the endoscope 815 can be at least slidably-attached to the distal end 808 of the outer tube 805 by inserting the endoscope 815 through a dedicated port (not shown) for the endoscope 815, such that the system 800 is configured to be substantially limited to a sliding movement in and out of the distal end 808 of the outer tube 805. And, in some embodiments, the endoscope 815 can be allowed to also float in a port 806a that is substantially larger than the endoscope 815, providing a sliding motion for the endoscope as well as room for side-to-side movements as well.

Figure 9A:
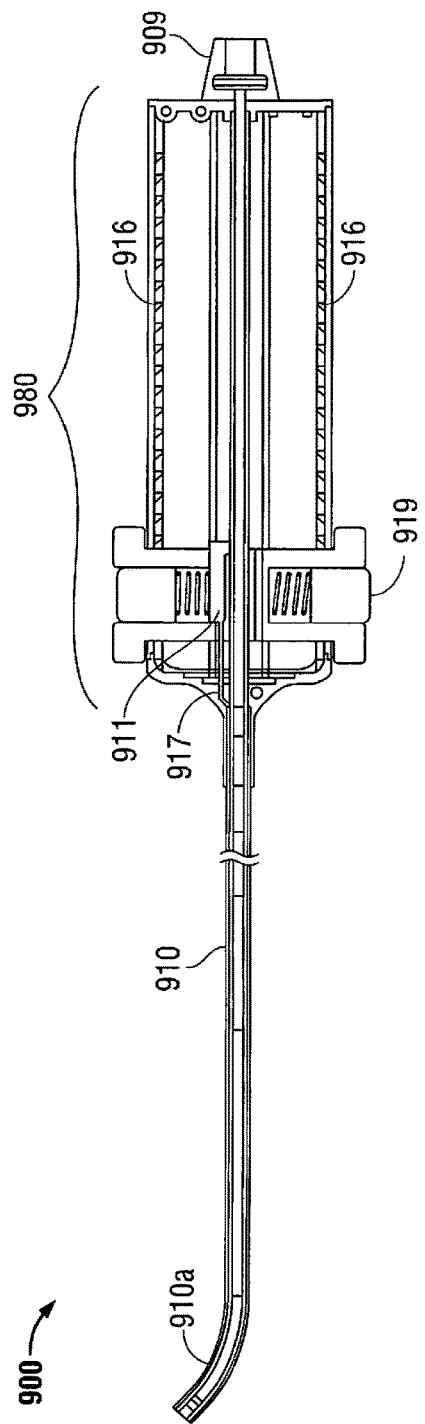
FIGS. 9A and 9B illustrate side views of working, and/or floating, channels that can be used to guide tools as taught herein, according to some embodiments.
Figure 9B:
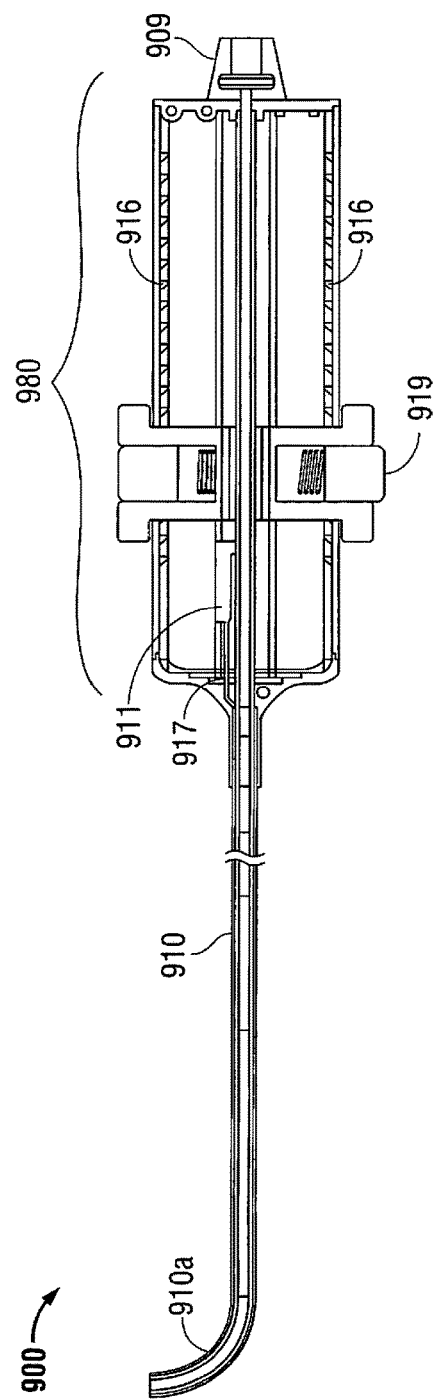

FIGS. 9A and 9B illustrate side views of working, and/or floating, channels that can be used to guide tools as taught herein, according to some embodiments. As discussed herein, the working channels can have at least a portion of which floats in the lumen of the outer tube in a manner that is the same or similar to FIG. 8 to further enhance the flexibility of the outer tube during position of the system in a subject. In some embodiments, the terms "channel," "floating channel," "working channel," and "tool channel" can be used interchangeably. Each working channel can be operatively connected to a handle 980 in a manner that is the same or similar to the operable connections taught herein for the retractor actuator and/or the stabilizer actuator. FIG. 9A shows the tip 910a of the working channel 910 in a substantially extended position, whereas FIG. 9B shows the tip 910a of the working channel 910 in a substantially bent position, such that the tip 910a is deflected substantially normal to the central axis of the working channel 910. A working channel system 900 consistent with other systems taught herein, for example, can include an entry port 908, a working channel 910, a wire coupler 911, ratchet teeth 916, a pull wire 917 for flexing or extending the tip 910a of the working channel 910, and wire actuator 919. The ability to flex the tip 910a of the working channel 910 facilitates independent positioning of a tool (not shown) in the treatment of a target tissue in a subject. In some embodiments, the wire actuator 919 can be multi-positional, having at least three positions for bending tip 910a of working channel 910. In some embodiments, the wire actuator 919 can have a plurality of ratchet teeth 916 to provide a plurality of positions for reversibly-fixing the bent tip 910a in position during use of the tool (not shown) in the treatment of the target tissue in the subject.

As described herein, the channels can be configured to control the trajectory and position of instruments such as forceps in the working space created by the retractor. In some embodiments, a channel can be removed from, or inserted through, the outer tube of the system, alone or inside an additional channel that may be used as a guide. The channels can be virtually any size considered by one of skill to be useful in the systems described herein. For example, a channel can have an inner diameter ranging from about 1 mm to about 5 mm, from about 2 mm to about 4 mm, from about 1 mm to about 3 mm, or any range therein. The length of the channel should, of course, complement the length of the system. For example, the channel can have a length ranging from about 40" to about 72", from about 48" to about 60", from about 42" to about 70", from about 44" to about 68", or any range therein in increments of 1".

The channels can also comprise any material or configuration known to one of skill to be suitable for the uses described herein. For example, the channels can comprise a single polymer layer, multiple polymer layers, a wire reinforced layer, or a combination thereof. In some embodiments, a channel can comprise (i) an inner layer of a polymer such as, for example TEFLON or polyethylene for slippery luminal surface on the inner diameter of the channel; (ii) a metal such as, for example, a stainless steel, nitinol, or cobalt chromium as a wire reinforcement in the configuration of a braid, mesh, or helical coil layer covering the inner layer; and, (iii) an outer layer of a polymer such as, for example, PEBAX, polyurethane, polyethylene, silicone, PVC, or nylon.

In some embodiments, the channels can be configured such that the outer layer (iv) is the most rigid in the proximal section of the channel (i.e., the first about 12" to about 24" of the channel), having a hardness of about 60 Shore D to about 80 Shore D; (v) has a medium stiffness in the middle section (i.e., the next about 12" to about 36" of the channel), having a hardness of about 50 Shore D to about 72 Shore D; and, (vi) is the most flexible in the distal section (i.e., the next about 0.5" to about 2" of the channel), having a hardness of about 20 Shore D to about 50 Shore D). The distal section of the channel can be the section that flexes and can be the distal about 1" of the channel, in some embodiments. In some embodiments, the channels can have a rigid section just proximal to the distal section to keep this flexible section straight when there is a bending moment on the tip such as when the instrument which is inserted through the channel is grasping a tissue during a gastrointestinal treatment, for example. The length of the rigid section of the channels can range, for example, from about 1 cm to about 10 cm, from about 2 cm to about 8 cm, from about 3 cm to about 7 cm, from about 4 cm to about 6 cm, about 6 cm, or any range therein in 1 cm increments. The rigid section can include a rigid tube comprising a reinforcement material such as, for example, stainless steel or NITINOL, or a polymer such as PEEK or a polyimide embedded between the outer polymer layer and the inner polymer layer. The rigid section can have any suitable length to perform it's function in the system. In some embodiments, the rigid section can have a length ranging from about 0.001" to about 0.005".

The thickness of the inner layer of the channels can range from about 0.0005" to about 0.005", from about 0.001" to about 0.004", from about 0.002" to about 0.003", about 0.001", or any range therein in 0.0005" increments. The thickness of the reinforcement layer can range from about 0.001" to about 0.006," from about 0.002" to about 0.005," from about 0.003" to about 0.005," from about 0.001" to about 0.003," about 0.002", or any range therein in increments of 0.0005". The thickness of the outer layer can range from about 0.003" to about 0.012", from about 0.004" to about 0.010," from about 0.005" to about 0.009," from about 0.005" to about 0.008," about 0.010", or any range therein in increments of 0.001".

For flexing the distal end of the channel, there can be a side lumen with a pull wire embedded between the inner layer and the outer layer. In some embodiments, the side lumen can be located between the inner layer and the reinforcement layer, or the side lumen can be a part of the inner layer. The side lumen can be made of any material considered by one of skill to be useful in the systems taught herein. For example, the material can include a flexible tube of polymer such as, for example, TEFLON or polyethylene. In some embodiments, the side lumen runs parallel to the length of the channel in the distal section of the channel and then helical proximal to the distal section of the channel. The pitch of the helix can vary, for example, from about 1.0" to about 6.0", from about 2.0" to about 5.0", from about 1.0" to about 4.0", from about 3.0" to about 5.0", about 4.0", or any range therein in 0.1" increments. By routing the side lumen helically, the wire tension can be distributed all around the shaft so that the shaft can be rotated in any orientation smoothly and remain at least substantially stable. In some embodiments, the pull wire can run from the wire actuator in the handle into the side lumen, out of the distal end of the side lumen, and looped around a rigid ring. The rigid ring (stainless steel, 0.002-0.005" thick, 0.040"–0.25" long) at the distal end and back into the side lumen and out into the handle and attached to the wire actuator. The handle can be operatively connected to the channel, the handle having a housing, and a lumen in communication with the channel. The wire actuator is operatively attached to the pull-wire inside the housing with a button on the outside of the handle allowing the wire actuator to slide back (proximal) and forth (distal) on the handle to pull and push the pull-wire. Pulling the wire makes the tip flex and become rigid, whereas pushing the wire can make the tip relax and straighten. The slide has a means for locking the wire actuator in place, for example, using complementary ratchet teeth on the housing and wire actuator mechanism. When the wire actuator button is pressed, the ratchet teeth can disengage and unlock the pull-wire. In some embodiments, the tip can flex from about 0 degrees to about 150 degrees. In another embodiment, the tip can flexed from about 45 degrees to about 100 degrees. The can be designed to be flexible in bending but stiff in torsion, allowing the channel to follow the curvatures of the anatomy and allow for a rotation of the handle from outside the body during use, transmitting torque to rotate the tip to a desired direction.

The working channels positioned inside the outer tube provide a multi-lumen catheter having manipulable passages for independently manipulating tools from outside the body into the working space inside created by expansion of the retractor. In some embodiments, from 1 to 3 flexible tubes run inside of the outer tube and can be detached from the outer tube, as described herein, which facilitates the flexibility of the system. In some embodiments, these flexible tubes can be attached at two points: (i) the proximal coupler of the retractor, which can be a ring-type structure having ports at the distal end of the outer tube, and (ii) at the proximal end of the shaft, such as at the handle. This can provide a floating arrangement in the outer tube that is unique, constraining the ends of the flexible tubes while allowing for a substantially free-floating movement of the flexible tubes in the outer tube to enhance the flexibility of the system.

In some embodiments, 2 inner tubes can be positioned adjacent to the inner surface of the outer tube to provide, effectively, 3 separate channels. The 2 inner tubes can function as 2 independent working channels while the space between these first 2 working channels and the outer tube functions as a third channel. The third channel can be substantially larger than the other 2 channels. Each of the first 2 working channels can have, for example, an inner diameter ranging from about 2 mm to about 6 mm, about 3 mm to about 5 mm, or any range therein. In some embodiments, the diameter of the first 2 working channels can be about 4 mm. Each of the channels can be designed to accommodate an endoscope such as a colonoscope, as well as tools that include, for example, forceps, graspers, clip applier, dissectors, snares, electrical surgical probes, or loops. In some embodiments, the largest diameter channel can be the channel for the endoscope.

The channel for accommodating the endoscope can be designed to have an inner diameter, for example, ranging from about 5 mm to about 15 mm, from about 6 mm to about 12 mm, from about 11 mm to about 14 mm, from about 5 mm to about 10 mm, from about 8 mm to about 13 mm, or any range therein in 1 mm increments. The inner tubes can comprise any suitable material known to one of skill to be useful for the purposes set-forth herein, as well as composites thereof. For example, the inner tubes can comprises a fluoropolymer such as TEFLON for lubricity to ease tool or endoscope passage and movements. Other materials that may be used include, for example, polyethylene, polypropylene, PEBAX, nylon, polyurethane, silicone, and composites thereof, each of which may also be used with a lubricant coating. The tubes may also comprise a metallic wire reinforcement such as a braid, mesh or helical coil, each of which may be embedded in the tube.

One of skill should appreciate that the systems taught herein can be used as a surgical suite with a floating, multi-lumen-catheter retractor system having a reversibly-stabilized and reversibly-expandable retractor for a minimally invasive treatment of a subject. In these embodiments, the system can comprise a flexible outer tube for guiding a floating channel and a floating endoscope in a substantially floating arrangement within the system. Due to the construction of the floating system, the system is highly flexible, such that the flexible outer tube can be highly flexible and have a lumen, a proximal end, and a distal end; and, the floating channel can serve as a guide through which a tool is manipulated in a treatment of a target tissue in a subject. The retractor can be a reversibly-stabilized and reversibly-expandable retractor forming a treatment space upon expansion. The retractor can be configured, for example, for the expansion to occur distal to the distal end of the outer tube and to reversibly stiffen an otherwise flexible arrangement of the retractor, the flexible arrangement designed to facilitate the positioning of the system in the subject and to reversibly stiffen for the expansion of the retractor.

During a use of the system, the floating channel can be (i) at least slidably-attached to the lumen of the outer tube at a first proximal location and a first distal location and (ii) at least substantially floating in the lumen of the outer tube between the first proximal location and the first distal location. Likewise, during the use of the system, the floating endoscope can be (iii) at least slidably-attached to the lumen of the outer tube at a second proximal location and a second distal location; and, (iv) at least substantially floating in the lumen of the outer tube between the second proximal location and second distal location. And, during the use of the system, the floating arrangement can (v) at least substantially increase the flexibility of the system over a second such system having lumens for a tool and an endoscope, the lumens affixed to the lumen of the outer tube throughout the length between the proximal end and the distal end of the outer tube. The increased flexibility can facilitate an ease of positioning of the system in the subject; and, the reversibly-stiffened arrangement of the retractor can form an at least substantially rigid beam as a structural support for the expansion in the subject for the treatment of the target tissue.

In some embodiments, the retractor comprises at least two expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a distal nexus located distal to the distal end of the outer tube and at which the distal end of each of the at least two retractor elements is affixed; and, a stabilizer subsystem connecting the distal nexus to the distal end of the outer tube and having an at least substantially rigid component configured to reversibly stiffen an otherwise flexible portion of the retractor for an asymmetric expansion of the retractor.

In some embodiments, the retractor comprises four expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a proximal coupler attached to the distal end of the outer tube, the proximal coupler having four retractor ports for the slidable engagement with the four retractor elements, the four retractor ports positioned circumferentially around the proximal coupler and configured to facilitate a reversible, axial sliding of the retractor elements for the asymmetric expansion of the retractor. These embodiments can also include a distal nexus located distal to the distal end of the outer tube and at which the distal ends of each of the four retractor elements are affixed; and, a stabilizer subsystem connecting the distal nexus to the distal end of the outer tube and having (i) a flexible component that extends from the proximal coupler to the distal nexus and (ii) an at least substantially rigid component that is slidably engaged with the proximal coupler and reversibly extends from the proximal coupler to the distal nexus to reversibly-stiffen the retractor in an asymmetric expansion of the retractor.

The flexible component and the rigid component can have central axes that are each at least substantially parallel to the central axis of the distal end of the shaft, the rigid component forming an at least substantially rigid beam as a structural support for the asymmetric expansion, the rigid beam having a luminal side and an abluminal side.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; treating the lesion with the tool; collapsing the retractor; and, withdrawing the system from the subject. The lesion can include, for example, a perforation, a tissue pathology a polyp, a tumor, a cancerous tissue, a bleed, a diverticuli, an ulcer, an abnormal vessel, or an appendix.

It should be appreciated that there are a number of procedures and variations, in addition to those taught above, that can be used readily by one of skill in the implementation of the systems taught herein. In some embodiments, one of skill can insert the endoscope through the endoscope channel of the system and extend the distal end of the endoscope distal to the distal end of the retractor to form an assembly. The assembly can then be inserted into a body lumen or orifice, such as the colon, and advanced orally until the distal end of the scope or the lens is in proximity to the target tissue (lesion or defect) to be treated. The system is advanced forward over the scope until the retractor is positioned over the distal end of the endoscope while observing the image from the endoscope. The system is advanced until the target tissue is located between the proximal coupler and distal nexus of the retractor while observing the image from the endoscope. The handle or outer tube can be rotated to rotate the retractor so that the target tissue is at the desired position relative to the retractor members while observing the image from the endoscope. The retractor can then be straightened and stabilized by converting the flexible beam to a rigid beam. The retractor can then be expanded by moving the retraction actuator forward on the handle while observing the image from the endoscope. This action pushes the tissue outwards, creates a working space around the target tissue, and anchors and stabilizes the target tissue. Optionally, while the retractor is expanded, the system can be pulled back to shift the peak of the most expanded members distally to improve working distance between the endoscope and the peak of the asymmetric work space, wherein the peak is generally recommended to be located around the target tissue. With the instruments inserted into the working channels, insert the working channels into the proximal ports of the system and advance the instruments and channels distally until the tips of the working channels are distal to proximal coupler of the retractor while observing the image from the endoscope. At this time, the tips of the working channels can be flexed to the appropriate angulation for the tools to approach the lesion to be treated. The working channels can be rotated and moved axially as needed to the desired position for the tools. Likewise, the instruments/tools can be advanced relative to the distal end of the working channels as needed to extend the instruments as needed to reach the target tissue. Various instruments can be inserted through the working channels as desired, and both the endoscope and the instruments can be advanced and positioned independently into the working area to further manipulate and visualize the target tissue at closer proximities or angulations. This is because, in some embodiments, the endoscope can also flex within the working space.

In some embodiments, it's desirable to have a means for delivering a system taught herein with an optional cover, or sheath that covers a portion of the system, including the retractor during delivery of the retractor to a target site, during a treatment of a target tissue at the target site, during a removal of the target tissue, during a removal of the system from the subject, or a combination thereof. Recall that some embodiments of such an optional cover 355 have been illustrated herein, for example, in FIGS. 3A and 3K. One of skill will appreciate that the retractor has elements that can catch, snag, or otherwise disturb or contact tissue during delivery, or removal, of the retractor to or from the target site. Also, the treatment of the target tissue may include, for example a dissection of tissue that can be performed within the cover without or intermingling the target tissue with the surrounding tissues. Moreover, the dissected tissue may be a cancerous tissue that is desirable to contain during treatment or removal. The terms "cover" and "sheath" can be used interchangeably in many embodiments, and one of skill can appreciate that such embodiments are open to improvements, as taught herein.

Figure 10A:
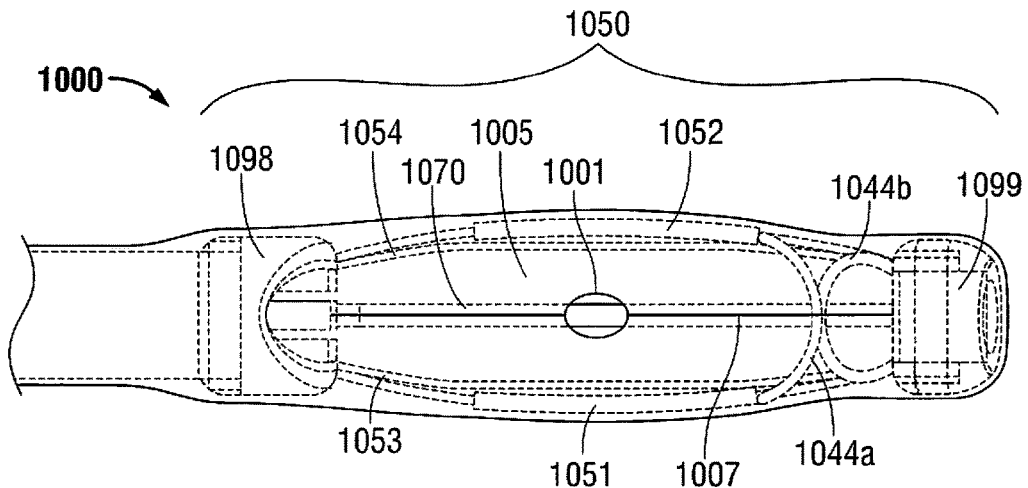
FIGS. 10A-10E illustrate a retractor sheath covering a retractor of a system as taught herein, according to some embodiments.
Figure 10B:
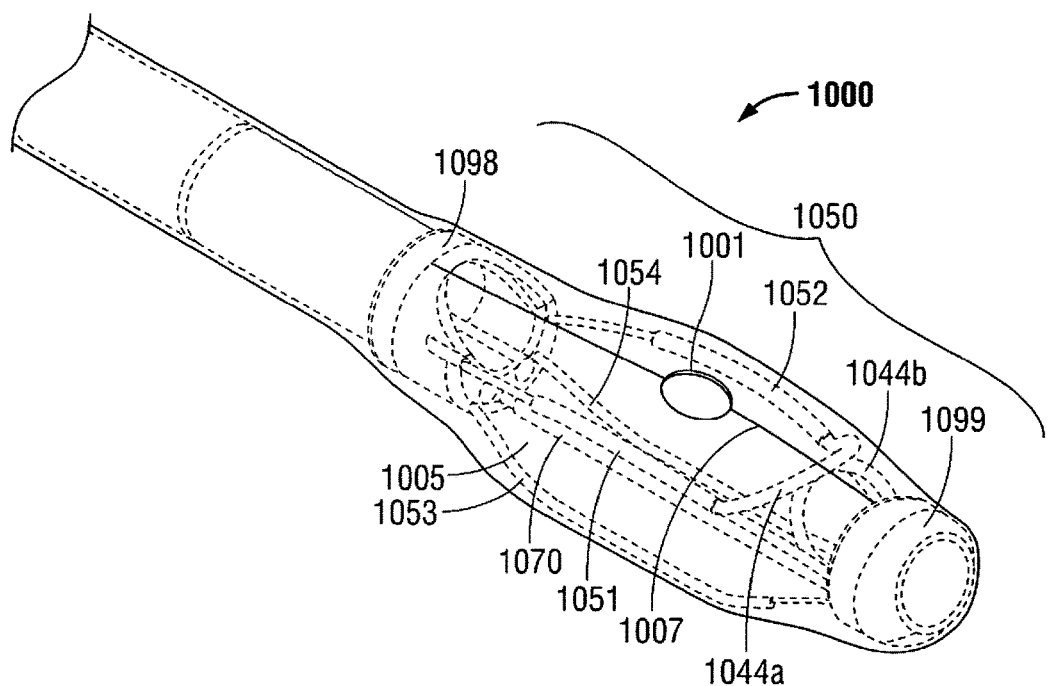
Figure 10C:
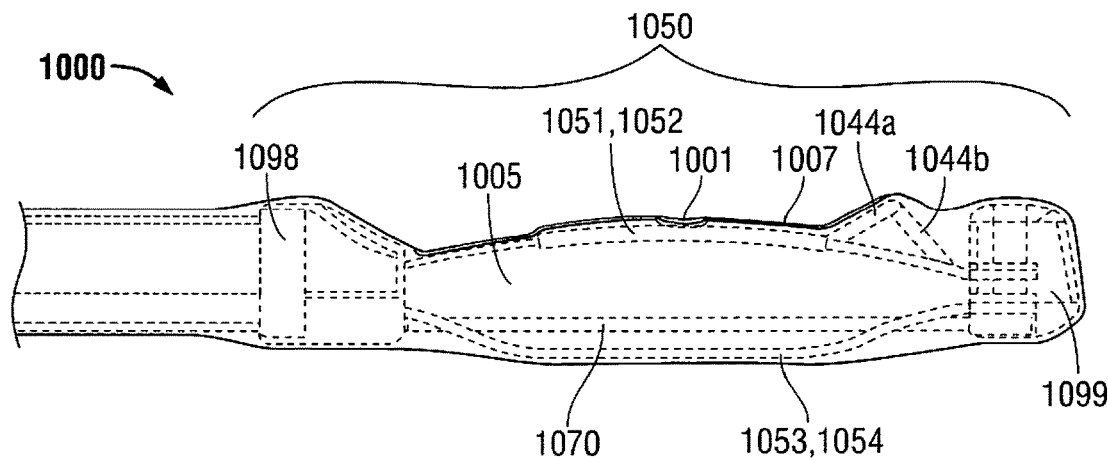
Figure 10D:
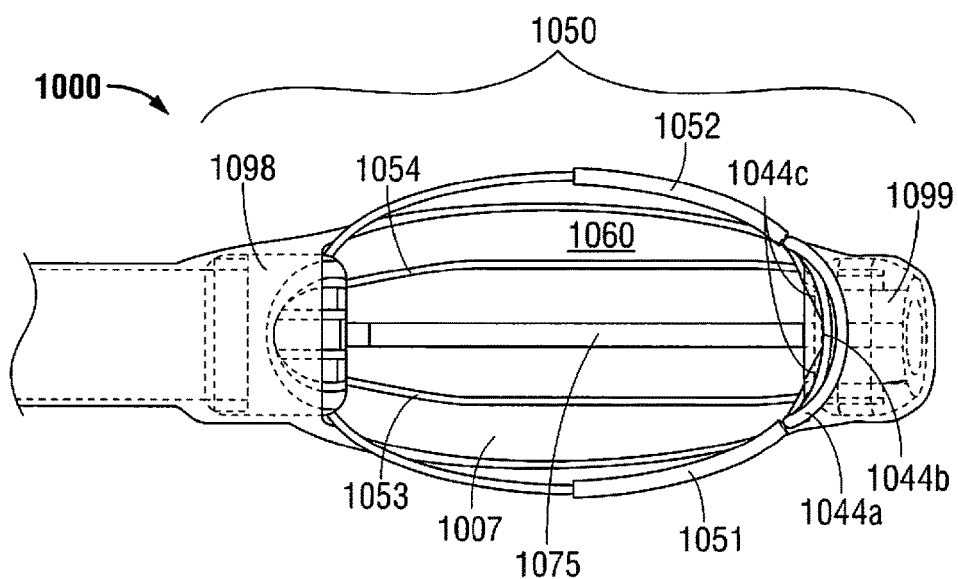
Figure 10E:
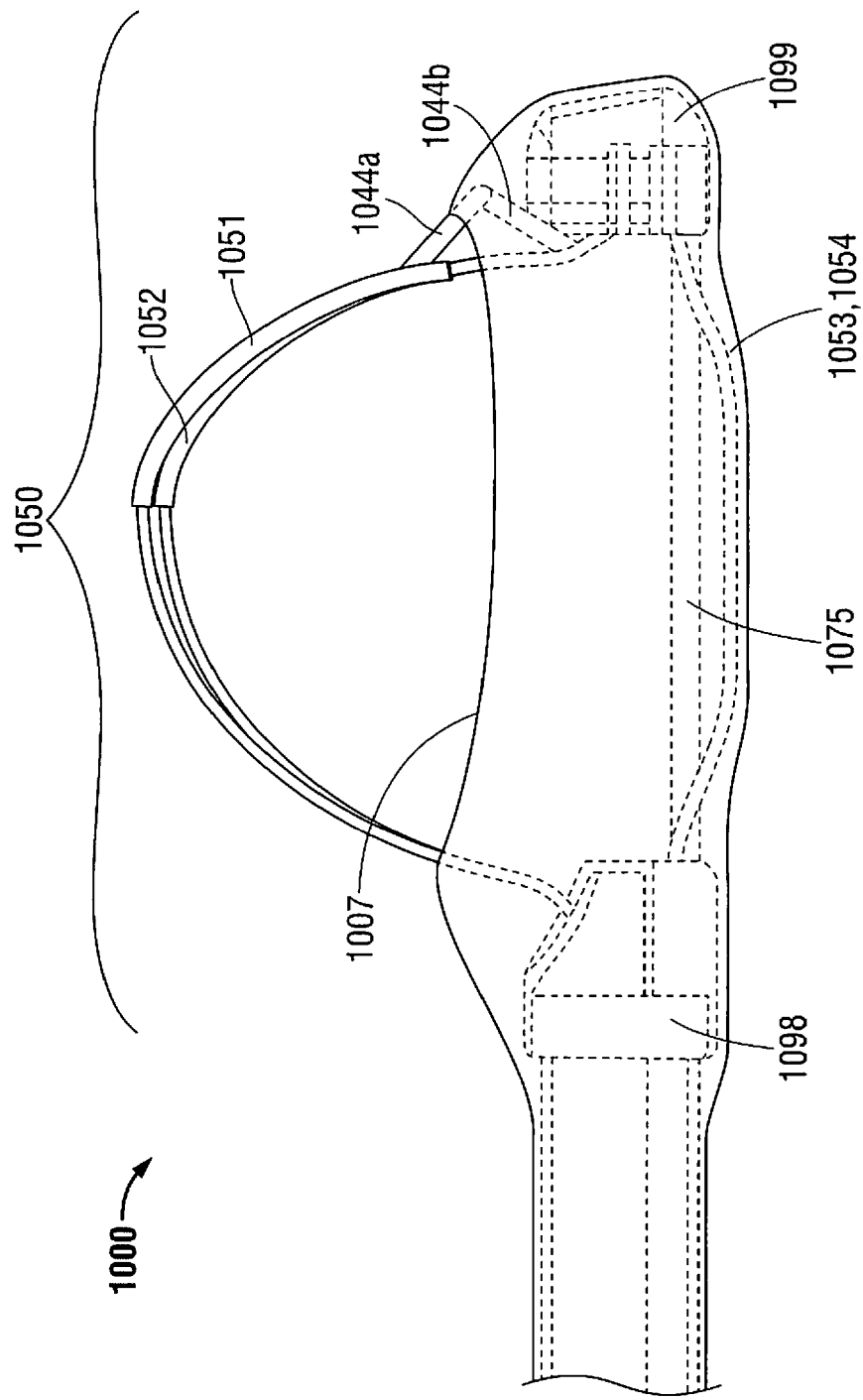

FIGS. 10A-10E illustrate a retractor sheath covering a retractor of a system as taught herein, according to some embodiments. FIGS. 10A-10C show top-, oblique-, and side-views a flexible, clear sheath 1000 that covers a collapsed configuration of the retractor 1050 to render an at least substantially smooth and/or atraumatic surface 1005 for a delivery of the retractor 1050 to a target site (not shown) for a treatment of a target tissue (not shown). In FIGS. 10A-10C, the cover is in a closed configuration that can be sustained until the expansion of the retractor 1050 for the treatment, or it can be reversibly-obtained following the treatment. FIGS. 10D and 10E show a top-view and side-view of an expanded configuration of the retractor with the cover in an open configuration for the treatment.

The sheath 1000 can be designed to prevent or inhibit the retractor elements 1051, 1052, 1053, 1054 and bridges 1044a, 1044b from catching, snagging, or otherwise disturbing or contacting tissue during a delivery or removal of the retractor 1050 to or from the target site. Note also, optional bridge retainer 1044c used in operable connection with upper bridge 1044a, for example. Such retainers can be used at any position around the retractor to facilitate a retention of the configuration of the working space 1060, for example, to retain the configuration under forces of the expansion of the retractor 1050. During the procedure the sheath 1050 can also prevent or inhibit tissue from entering the retractor 1050 until desired. The sheath 1050 can also act as a collection means for entrapping and/or pulling out a resected tissue, which can be particularly desirable in the resection of cancerous tissue in some embodiments. The sheath 1000 can be at least substantially closed around the retractor 1050 during delivery, and can be designed to open as the retractor 1050 is expanded to create the working space 1060 for the treatment. As described herein, flexible beam 1070 can be converted to the at least substantially rigid beam 1075 using a means for the conversion as taught herein, for the expansion.

In some embodiments, the sheath 1000 can be perforated longitudinally (not shown), designed such that the sheath 1000 opens upon expansion of the retractor 1050 through tearing of the perforation at the target site. In some embodiments, a tongue-and-groove mechanism, for example a ZIPLOCK mechanism, can be used to at least substantially close a slit 1007 at the top of the retractor 1050 which can also open upon the expansion of the retractor 1050 at the target site. In some embodiments, a larger perforation, or unclosed portion 1001, can remain in the sheath 1000 to facilitate the tearing or opening of the sheath at the target site upon the expansion of the retractor 1050. In some embodiments, the terms "slit" and "opening" can be used interchangeably.

In some embodiments, the sheath can be reversibly opened, such that the sheath can be re-closable. For example, a drawstring, cable, or wire, can be operably positioned in communication with the opening for the re-closing of the opening by pulling or pushing the drawstring, cable, or wire from outside the patient during the treatment. In some embodiments, the edges of the opening can form longitudinal pockets or channels for pulling or pushing the drawstring, cable, or wire as desired from outside the patient during the treatment, such as by routing the drawstring, cable, or wire through the system and, perhaps, through the handle as with the other actuation means. In some embodiments, a drawstring is used to re-close the sheath, wherein the strings can be tensioned at the handle to close the slit, or loosened to allow the retractor to expand. In some embodiments, the sheath has a stiffening strip running transversely around the midportion of the cage to facilitate the cage wires expanding without catching on the surrounding sheath. The stiffening strip can be another layer of the sheath welded or glued onto the existing sheath. It can also be formed as a thickened area. Alternatively, a stiffer material can be inserted in the pocket running transversely. The stiffening material may be the same as that of the sheath or it may be a stiffer material.

One of skill will appreciate that any of the known materials and/or methods of covering the sheath may be useful for the purposes taught herein. For example, the sheath can range from about 10 mm to about 30 mm at the ends that are attached to the proximal coupler and distal nexus, each of which can be used to define the ends of the retractor 1050. Moreover, the sheath can be heat welded, glued, or heat-shrunk to the proximal coupler and/or distal nexus, or perhaps substantially proximal or distal to these components, to fasten the sheath to the retractor. In some embodiments, the sheath may even cover the system as a sterilizing, or clean, cover, such that the sheath is an extension of a disposable and/or replaceable component that may be applied, for example, in a sterilization process. And, in some embodiments, the sheath can be larger at the mid portion where the diameter can range, for example, from about 20 mm to about 40 mm in a closed configuration. The sheath can be, for example, opaque, translucent, or clear, and the material composing the sheath can be, for example, a polyethylene, nylon, fluorinated ethylene propylene (FEP), TEFLON, polyethylene terephthalate (PET), or polycarbonate. And, in some embodiments, the sheath material can range, for example, from about 0.0010" to about 0.0060" thick, from about 0.0020 to about 0.0080" thick, from about 0.0030" to about 0.0050" thick, from about 0.0010" to about 0.0030" thick, from about 0.0005" to about 0.0100" thick, about 0.0020" thick, or any range therein in about 0.0005" increments.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

We claim:

1. A method, comprising:
inserting an endoluminal device comprising a flexible tubular member and a chamber into a gastrointestinal tract, wherein the chamber includes first and second flexible elements connected by a bridge member;
visualizing a portion of the gastrointestinal tract;
expanding the first and second flexible elements against a wall of the gastrointestinal tract to create a working space within the gastrointestinal tract;
inserting first and second instruments through the tubular member;
angling a first tip of the first instrument and a second tip of the second instrument within the chamber toward a lesion within the gastrointestinal tract, wherein the first and second tips are movable independent of each other;
removing at least a portion of the lesion;
capturing the removed portion of the lesion within the chamber, wherein the chamber is at least partially enclosed to receive the lesion; and removing the endoluminal device and captured lesion from the gastrointestinal tract.

2. The method of claim 1, wherein the chamber further includes third and fourth flexible elements.

3. The method of claim 2, further comprising stiffening at least one of the third or fourth flexible elements to increase the stability of the chamber.

4. The method of claim 2, wherein a distal end of each of the first, second, third and fourth flexible elements is fixed.

5. The method of claim 4, wherein an articulating endoscope is positioned within the endoluminal device, and the distal end of each of the first, second, third and fourth flexible elements extends distally beyond a distal tip of the articulating endoscope.

6. The method of claim 1, wherein the endoluminal device includes an actuator and the method further comprises moving the actuator to move the chamber between a collapsed and expanded configuration.

7. The method of claim 1, wherein the chamber expands distally beyond a distal end of the flexible tubular member.

8. The method of claim 1, wherein the expanded chamber comprises an asymmetric configuration.

9. The method of claim 1, wherein the bridge member is flexible and extends between the first and second flexible elements to increase the stability of the chamber.

10. The method of claim 9, wherein the bridge member is configured to prevent the first and second flexible elements from moving away from each other.

11. A method, comprising:
    inserting an endoluminal device comprising a flexible tubular member and a chamber into a gastrointestinal tract;
    visualizing a portion of the gastrointestinal tract;
    expanding the chamber against a wall of the gastrointestinal tract to create a working space, wherein the chamber comprises first and second flexible elements connected by a bridge member, and expanding the chamber comprises expanding the first and second flexible elements;
    angling a first tip of a first instrument and a second tip of a second instrument within the chamber toward a lesion within the gastrointestinal tract;
    the first and second tips being movable independent of each other;
    removing at least a portion of the lesion;
    capturing the removed portion of the lesion within the chamber; and
    removing the endoluminal device and captured lesion from the gastrointestinal tract.

12. The method of claim 1, wherein the expanded chamber comprises an asymmetric configuration that defines the working space.

13. The method of claim 11, wherein the gastrointestinal tract is the colon.

14. The method of claim 11, wherein expanding the chamber applies a force against a wall of the gastrointestinal tract.

15. The method of claim 11, wherein the working space enables triangulation of the first and second instruments within the gastrointestinal tract.

* * * * *